US010562888B2

(12) United States Patent
Moniz et al.

(10) Patent No.: US 10,562,888 B2
(45) Date of Patent: Feb. 18, 2020

(54) CRYSTALLINE FGFR4 INHIBITOR COMPOUND AND USES THEREOF

(71) Applicant: Eisai R&D Management Co., Ltd., Tokyo (JP)

(72) Inventors: George Moniz, Cambridge, MA (US); Kristen Sanders, Gilmanton, NH (US); Arani Chanda, Andover, MA (US); Kenshi Yoshida, Tsukuba (JP)

(73) Assignee: Eisai R&D Management Co., LTD., Tokyo (JP)

( * ) Notice: Subject to any disclaimer, the term of this patent is extended or adjusted under 35 U.S.C. 154(b) by 0 days.

(21) Appl. No.: 15/566,527

(22) PCT Filed: Apr. 13, 2016

(86) PCT No.: PCT/US2016/027334
§ 371 (c)(1),
(2) Date: Oct. 13, 2017

(87) PCT Pub. No.: WO2016/168331
PCT Pub. Date: Oct. 20, 2016

(65) Prior Publication Data
US 2018/0093972 A1  Apr. 5, 2018

Related U.S. Application Data

(60) Provisional application No. 62/147,313, filed on Apr. 14, 2015.

(51) Int. Cl.
C07D 403/12 (2006.01)
A61K 31/505 (2006.01)

(52) U.S. Cl.
CPC .......... *C07D 403/12* (2013.01); *A61K 31/505* (2013.01)

(58) Field of Classification Search
CPC ................................................ C07D 403/12
See application file for complete search history.

(56) References Cited

U.S. PATENT DOCUMENTS

| | | | |
|---|---|---|---|
| 7,371,750 B2 | 5/2008 | Sim et al. | |
| 7,501,425 B1 | 3/2009 | Dobrusin et al. | |
| 8,552,002 B2 | 10/2013 | Ding et al. | |
| 9,434,697 B2 * | 9/2016 | Reynolds | C07D 405/12 |
| 9,730,931 B2 * | 8/2017 | Reynolds | C07D 405/12 |
| 2010/0120773 A1 | 5/2010 | Guagnano et al. | |
| 2010/0143386 A1 | 6/2010 | Ullrich et al. | |
| 2013/0040949 A1 | 2/2013 | Gray et al. | |
| 2013/0137708 A1 | 5/2013 | Garske et al. | |
| 2013/0183294 A1 | 7/2013 | Pai et al. | |
| 2014/0088100 A1 | 3/2014 | Bifulco et al. | |
| 2014/0142084 A1 | 5/2014 | Kameda et al. | |
| 2014/0296216 A1 | 10/2014 | Ding et al. | |
| 2016/0130237 A1 * | 5/2016 | Reynolds | C07D 405/12 514/235.8 |
| 2017/0007601 A1 * | 1/2017 | Reynolds | C07D 405/12 |
| 2017/0360785 A1 * | 12/2017 | Reynolds | C07D 405/12 |
| 2018/0093972 A1 * | 4/2018 | Moniz | C07D 403/12 |

FOREIGN PATENT DOCUMENTS

| | | | | |
|---|---|---|---|---|
| WO | | 2006000420 A1 | 1/2006 | |
| WO | WO | 2006/000420 A1 | 1/2006 | |
| WO | | 2006038112 A1 | 4/2006 | |
| WO | | 2007071752 A2 | 6/2007 | |
| WO | | 2009158571 | 12/2009 | |
| WO | | 2011071821 A1 | 6/2011 | |
| WO | | 2011088196 A2 | 7/2011 | |
| WO | | 2012136732 A1 | 10/2012 | |
| WO | | 2012167415 A1 | 12/2012 | |
| WO | | 2014011900 A2 | 1/2014 | |
| WO | | 2014144737 A1 | 9/2014 | |
| WO | | 2014149164 A1 | 9/2014 | |
| WO | | 20150006492 A1 | 1/2015 | |
| WO | | 2015030021 A1 | 3/2015 | |
| WO | | 2015057938 A1 | 4/2015 | |
| WO | | 2015057963 A1 | 4/2015 | |
| WO | | 2015061572 A1 | 4/2015 | |
| WO | WO | 2015/057938 A1 | 4/2015 | |
| WO | | WO-2015057938 A1 * | 4/2015 | ........... C07D 405/12 |
| WO | | WO-2015057963 A1 * | 4/2015 | ........... C07D 405/12 |
| WO | | 2015108992 A1 | 7/2015 | |
| WO | | WO-2016168331 A1 * | 10/2016 | ........... C07D 239/48 |
| WO | | 2017198149 A1 | 11/2017 | |
| WO | | 2017198221 A1 | 11/2017 | |

OTHER PUBLICATIONS

S. Datta et al., 3 Nature Reviews | Drug Discovery, 42-57 (2004) ("Datta").*
A. Y. Lee et al., Annual Review of Chemical and Biomolecular Engineering (2011) (Year: 2011).*
F. Colombo et al., Xenobiotica (2019) (Year: 2019).*
Lima, et al., "Bioisosterism: A Useful Strategy for Molecular Modification and Drug Design", Current Medicinal Chem., 2005, pp. 23-49, vol. 12.
International Search Report (PCT/ISA/210) dated Jun. 10, 2016, by the European Patent Office as the International Searching Authority for International Application No. PCT/US2016/027334.
Written Opinion (PCT/ISA/237) dated Jun. 10, 2016, by the European Patent Office as the International Searching Authority for International Application No. PCT/US2016/027334.
Guagnano et al., "Discovery of 3-(2,6-Dichloro-3,5-dimethoxyphenyl)-1-{ 6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", Journal of Medicinal Chemistry, 2011, pp. 7066-7083, vol. 54.

(Continued)

*Primary Examiner* — Alexander R Pagano
(74) *Attorney, Agent, or Firm* — Buchanan Ingersoll & Rooney PC

(57) ABSTRACT

A number of crystalline forms of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide are provided. These include a crystalline free base form, a crystalline monohydrochloride salt form, a crystalline dihydrochloride salt form, and a crystalline ethanesulfonate salt form. Methods of making and using crystalline compounds are also provided.

3 Claims, 20 Drawing Sheets

(56) References Cited

OTHER PUBLICATIONS

International Search Report (PCT/ISA/210) dated Feb. 3, 2015, by the European Patent Office as the International Searching Authority for International Application No. PCT/US2014/060857.
Written Opinion (PCT/ISA/237) dated Feb. 3, 2015, by the European Patent Office as the International Searching Authority for International Application No. PCT/US2014/060857.
Guagnano et al., "Discovery of 3-(2.6-Dichloro-3.5-dimethoxyphenyl)-1-{6[4-(4-ethyl-piperazin-1-yl)-phenylamino] pyrimidin-4-yl}-1-methyl-urea(NVP-BGJ398). A Potent and Selective Inhibitor of the Fibroblast Growth Factor Receptor Family of Receptor Tyrosine Kinase", Journal of Medicinal Chemistry, Oct. 2011, pp. 7066-7083, vol. 54, No. 2.
Liew et al., "SVM Model for Virtual Screening of Lck Inhibitors", J. Chem. Inf. Model., 2009, pp. 877-885, vol. 49, No. 4.
Maier et al., "Development of N-4,6-pyrimidine-N-alkyl-N0-phenyl ureas as orally active inhibitors of lymphocyte specific tyrosine kinase", Bioorganic & Medicinal Chemistry Letters, 2006, pp. 3646-3650, vol. 16.
Anwer et al., "A QSAR Study on Some Series of Anticancer Tyrosine Kinase Inhibitors", Medicinal Chemistry, 2013, pp. 203-212, vol. 9, No. 2.
Tan et al., "Development of covalent inhibitors that can overcome resistance to first-generation FGFR kinase inhibitors", PNAS, Oct. 2014, pp. E4869-E4877.
Zhang et al., "Targeting cancer with small molecule kinase inhibitors", Nature Reviews/Cancer, Jan. 2009, pp. 28-39, vol. 9 (including one page of Supplementary Information).
Anastassiadis et al., "Comprehensive assay of kinase catalytic activity reveals features of kinase inhibitor selectivity", Nature Biotechnology, Nov. 2011, pp. 1039-1046, vol. 29, No. 11.
Brooks et al., "Molecular Pathways: Fibroblast growth factor signaling: a new therapeutic opportunity in cancer", Clinical Cancer Research, Mar. 2012, pp. 1-25.
Dieci et al., "Fibroblast Growth Factor Receptor Inhibitors as a Cancer Treatment: From a Biologic Rationale to Medical Perspectives", Cancer Discovery, Feb. 2013, pp. OF1-OF16.
French et al., "Targeting FGFR4 Inhibits Hepatocellular Carcinoma Preclinical Mouse Models", PLoS ONE, May 2012, pp. 1-12, vol. 7, issue 5.
Liu et al., "Developing Irreversible Inhibitors of the Protein Kinase Cysteinome", Chemistry & Biology Review, Feb. 2013, pp. 146-159, vol. 20.
Gavine et al., "AZD4547: An Orally Bioavailable, Potent, and Selective Inhibitor of the Fibroblast Growth Factor Receptor Tyrosine Kinase Family", Cancer Research, Feb. 2012, pp. 2045-2056, vol. 72, No. 8.
Olechno et al., "Improving IC50 Results with Acoustic Droplet Ejection", Technical Brief JALA, Aug. 2006, pp. 240-246.
Pelaez-Garcia et al., "FGFR4 Role in Epithelial-Mesenchymal Transition and Its Therapeutic Value in Colorectal cancer", PLOS ONE, May 2013, pp. 1-11, vol. 8, issue 5.
Santos et al., "Michael Acceptors as Cysteine Protease Inhibitors", Mini-Reviews in Medicinal Chemistry, 2007, pp. 1040-1050, vol. 7, No. 10.
Sawey et al., "Identification of a Therapeutic Strategy Targeting Amplified FGF19 in Liver Cancer by Oncogenomic Screening", Cancer Cell, pp. 347-358, Mar. 2011, vol. 19.
Wesche et al., "Fibroblast growth factors and their receptors in cancer", Biochem. Journal, 2011, pp. 199-213.
Yanochko et al., "Pan-FGFR Inhibition Leads to Blockade of FGF23 Signaling, Soft Tissue Mineralization, and Cardiovascular Dysfunction", Toxicological Sciences, Jul. 2013, pp. 1-14.
Zaid et al., "Identification of FGFR4 as a Potential Therapeutic Target for Advanced-Stage, High-Grade Serous Ovarian Cancer", Clinical Cancer Research, Jan. 2013, pp. 809-820, vol. 19, No. 4.
Zhao et al., "A Novel, Selective Inhibitor of Fibroblast Growth Factor Receptors That Shows a Potent Broad Spectrum of Antitumor Activity in Several Tumor Xenograft Models", Molecular Cancer Therapeutics, Sep. 2011, pp. 2200-2210, vol. 10, No. 11.
Hagel et al., "First Selective Small Molecule Inhibitor of FGFR4 for the Treatment of Hepatocellular Carcinomas with an Activated FGFR4 Signaling Pathway", American Association for Cancer Research Journal, Mar. 2015, pp. 1-26.
Xu et al., "FGFR4 Gly388Arg polymorphism contributes to prostate cancer development and progression: A meta-analysis of 2618 cases and 2305 controls", BMC Cancer, 2011, pp. 1-6.
Miura et al., "Fibroblast growth factor 19 expression correlates with tumor progression and poorer prognosis of hepatocellular carcinoma", BMC Cancer, 2012, pp. 1-15.
Boyd et al., "Data Display and Analysis Strategies for the NCI Disease-Oriented in Vitro Antitumor Drug Screen", Cytotoxic Anticancer Drugs: Models and Concepts for Drug Discovery and Development, 1992, pp. 11-34.
Streit et al., "FGFR4 Arg388 allele correlates with tumour thickness and FGFR4 protein expression with survival of melanoma patients", British Journal of Cancer, 1994, pp. 1879-1886, vol. 94, No. 12.
Ye et al., "Fibroblast Growth Factor Receptor 4 Regulates Proliferation and Antiapoptosis During Gastric Cancer Progression", Cancer, Dec. 2011, pp. 5304-5313.
Chiang et al., "Focal Gains of VEGFA and Molecular Classification of Hepatocellular Carcinoma", American Association for Cancer Research Journal, Aug. 2008, pp. 6779-6788.
Sia et al., "Integrative Molecular Analysis of Intrahepatic Cholangiocarcinoma Reveals 2 Classes That Have Different Outcomes", Gastroenterology, 2013, pp. 829-840, vol. 144, No. 4.
Motoda et al., "Overexpression of fibroblast growth factor receptor 4 in high-grade pancreatic intraepithelial neoplasia and pancreatic ductal adenocarcinoma", International Journal of Oncology, 2011, pp. 133-143, vol. 38.
Taylor VI et al., "Identification of FGFR4-activating mutations in human rhabdomyosarcomas that promote metastasis in xenotransplanted models", The Journal of Clinical Investigation, Nov. 2009, pp. 3395-3407, vol. 119, No. 11.
Monks et al., "Feasibility of a High-Flux Anticancer Drug Screen Using a Diverse Panel of Cultured Human Tumor Cell Lines", Articles, Jun. 1991, pp. 757-766, vol. 83, No. 11.
Berge et al., "Pharmaceutical Salts", Journal of Pharmaceutical Sciences, Jan. 1977, pp. 1-19, vol. 66, No. 1.
Barderas et al., "An optimized predictor panel for colorectal cancer diagnosis based on the combination of tumor-associated antigens obtained from protein and phage microarrays", Journal of Proteomics, 2012, pp. 4647-4655, vol. 75.
Fawdar et al., "Targeted genetic dependency screen facilitates identification of actionable mutations in FGFR4, MAP3K9, and PAK5 in lung cancer", PNAS, Jul. 2013, pp. 12426-12431, vol. 110, No. 30.
Office Action dated Apr. 18, 2017, in Chinese Application No. 201480056358.4.
Office Action dated Sep. 20, 2017, in Colombian Application No. 16097757.
JP 2017-553988—First Decision of Rejection; dated Mar. 28, 2018.
JP 2017-553988—First Decision of Rejection; dated Mar. 28, 2018—English Translation of OA.
Takashi Kojima, For more efficient selection of crystal form in drug development, Journal of Pharmaceutical Science and Technology, Japan, Sep. 1, 2008, vol. 68, No. 5, pp. 344-349.
JP 2017-553988—Amendment and Response to Decision of Rejection; dated Apr. 26, 2018.
JP 2017-553988—Amendment and Response to Decision of Rejection; dated Apr. 26, 2018—English Translation of Claims.
JP 2017-553988—Second Decision of Rejection; dated May 2, 2018.
JP 2017-553988—Second Decision of Rejection; dated May 2, 2018—English Translation of 2nd Decision.
JP 2017-553988—Request for Appeal, Amendment, and Reconsideration; dated Aug. 1, 2018.
JP 2017-553988—Request for Appeal, Amendment, and Reconsideration; dated Aug. 1, 2018—English Translation of Claims.
JP 2017-553988—Decision to Grant; dated Oct. 18, 2019.

(56) References Cited

OTHER PUBLICATIONS

Russian Office Action and Search Report for RU2017139246 dated Oct. 21, 2019 with English translation of Office Action.

\* cited by examiner

CRYSTALLINE FGFR4 INHIBITOR COMPOUND AND USES THEREOF

CROSS-REFERENCE TO RELATED APPLICATIONS

This application claims priority to U.S. Provisional Patent Application No. 62/147,313, filed on Apr. 14, 2015. That application is incorporated by reference herein.

BACKGROUND

Fibroblast growth factors (FGF) are a family of more than 20 structurally related proteins with a variety of biological activities. Their main receptors, the fibroblast growth factor receptors (FGFR1, FGFR2, FGFR3 and FGFR4), are a family of receptor tyrosine kinases that bind FGF and are involved in processes of cell proliferation and differentiation. Deregulation of FGFR signaling networks is implicated in a number of pathophysiological conditions, including many types of human cancers.

"Fibroblast Growth Factor Receptor 4" or "FGFR4" is known to regulate proliferation and antiapoptosis and is expressed or highly expressed in many cancers. See, e.g., Dieci et al. 2013, Cancer Discovery, 0F1-0F16. Studies have shown that expression of FGFR4 is predictive of a more aggressive phenotype of the cancer, and knockdown or reduction of FGFR4 expression serves to reduce proliferation and promote apoptosis. See, e.g., Wesche et al. 2011, Biochem J 437:199-213.

For example, FGFR4 expression or overexpression is associated with cancer aggressiveness in gastric cancer (Ye et al. 2011, Cancer, 5304-5313), prostate cancer (Xu et al. 2011, BMC Cancer, 11; 84), sarcoma such as rhabdomyosarcoma (Taylor V I et al. 2009, J Clin Invest, 119(11):3395-3407), skin cancer such as melanoma (Streit et al. 2006, British J Cancer, 94:1879-1886), liver cancer such as cholangiocarcinoma (Sia et al. 2013, Gastroenterology 144:829-840) and hepatocellular carcinoma (French et al. 2012, PLoS ONE 7(5): e367313; Miura et al. 2012, BMC Cancer 12:56; Chiang et al. 2008, Cancer Res 68(16):6779-6788; Sawey et al. 2011, Cancer Cell 19:347-358), pancreatic cancer such as pancreatic intraepithelial neoplasia and pancreatic ductal adenocarcinoma (Motoda et al. 2011, Int'l J Oncol 38:133-143), lung cancer such as non-small-cell lung cancer (Fawdar et al. 2013, PNAS 110(30): 12426-12431), colorectal cancer (Pelaez-Garcia et al. 2013, PLoS ONE 8(5): e63695; Barderas et al. 2012, J Proteomics 75:4647-4655), and ovarian cancer (Zaid et al. 2013, Clin Cancer Res 19:809-820).

Clinical development of several FGFR inhibitors have confirmed their utility as antitumor agents. Dieci et al. 2013, Cancer Discovery, 0F1-0F16. However, new agents are needed that are useful to target FGFR, and FGFR4, in particular.

Furthermore, in the manufacture of pharmaceutical products, the compound should be in a form that can be conveniently manipulated and processed. In this regard, chemical stability and physical stability of the active compound are important considerations. Preferably, the compound and pharmaceutical compositions containing it are capable of being effectively stored over long periods of time without exhibiting significant change in physico-chemical characteristics.

SUMMARY

Embodiments of the invention may provide a crystalline form of the compound:

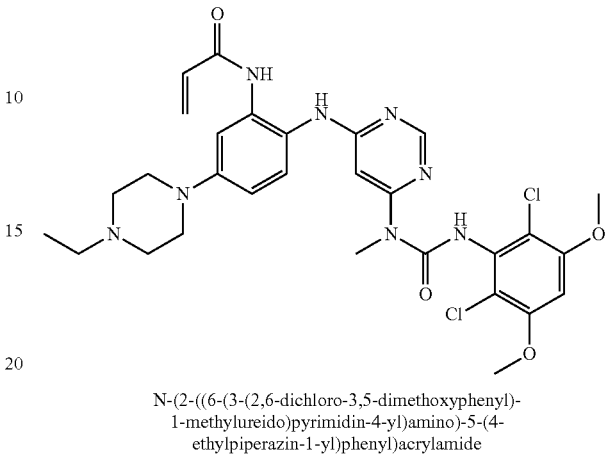

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide In some embodiments, for example, a crystalline form may be a free base form, a hydrochloride salt form, a monohydrochloride salt form, a dihydrochloride salt form, or an ethanesulfonate salt form.

Embodiments may provide a crystalline free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide (Compound 108):

(Compound 108)

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide In some embodiments, the crystalline free base form compound gives peaks in a powder X-ray diffraction (PXRD) spectra at least one, two, three, four, five or six of the following value ranges of 2θ°: 7.8-8.2; 10.1-10.5; 14.6-15.0; 16.3-16.7; 16.9-17.3; and 21.6-22.0. For example, the compound may exhibit at least one, two, three, four, five or six values of 2θ° (±0.2°) selected from the group consisting of: 8.0, 10.3, 14.8, 16.5 17.1 and 21.8. In some embodiments, the crystalline free base form compound is characterized by a PXRD pattern substantially as indicated in FIG. 5 (FIG. 5). In some embodiments the crystalline free base form of the compound gives peaks in powder X-ray diffraction spectra at the following ranges of 2θ° (±0.2): at least 10.3, 8.0 and 9.5; at least 10.3, 8.0, 9.5, 14.8, 16.5, and 17.1; or at least 10.3, 8.0, 9.5, 14.8, 16.5, 17.1, 19.3, 21.8, 23.7, and 24.5.

In some embodiments, the crystalline free base form is characterized by a differential scanning calorimetry (DSC) curve substantially the same as shown in FIG. 7 (FIG. 7).

In some embodiments, the crystalline free base form compound is characterized by a $^{13}$C NMR substantially as shown in FIG. 10 (FIG. 10).

Some embodiments may provide a compound that is a crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride salt gives peaks in powder X-ray diffraction spectra at the following ranges of 2θ° (±0.2): at least 26.6, 19.9, and 11.3; at least 26.6, 19.9, 11.3, 9.0, 23.5, and 25.4; or at least 26.6, 19.9, 11.3, 9.0, 23.5, 25.4, 27.6, 23.0, 18.1, and 29.0. In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl 1)phenyl)acrylamide monohydrochloride salt is characterized by a PXRD spectrum substantially as shown in FIG. 13 (FIG. 13).

In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride salt is characterized by a $^{13}$C NMR substantially as shown in FIG. 11 (FIG. 11).

Some embodiments may provide a compound that is a crystalline form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt gives peaks in powder X-ray diffraction spectra at the following ranges of 2θ° (±0.2): at least 26.6, 22.8, and 21.3; at least 26.6, 22.8, 21.3, 8.0, 26.2, and 13.5; or at least 26.6, 22.8, 21.3, 8.0, 26.2, 13.5, 12.4, 16.1, 28.0, and 18.7. In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt is characterized by a PXRD spectrum substantially as shown in FIG. 16 (FIG. 16).

In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt is characterized by a $^{13}$C NMR substantially as shown in FIG. 14 (FIG. 14).

Embodiments may provide a compound that is a crystalline form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt gives peaks in powder X-ray diffraction spectra at the following ranges of 2θ° (±0.2): at least 19.2, 15.1, and 23.3; at least 19.2, 15.1, 23.3, 20.3, 11.2, and 21.8; or at least 19.2, 15.1, 23.3, 20.3, 11.2, 21.8, 9.4, 22.4, 23.6, and 24.0. In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt is characterized by a PXRD spectrum substantially as shown in FIG. 19 (FIG. 19).

In some embodiments, the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt is characterized by a $^{13}$C NMR substantially as shown in FIG. 17 (FIG. 17).

A further purpose is a pharmaceutical composition comprising a crystalline form compound as described herein and a pharmaceutically acceptable carrier. In some embodiments, the composition is formulated for oral or parenteral administration.

A further purpose is a method of making a crystalline free base form of the compound:

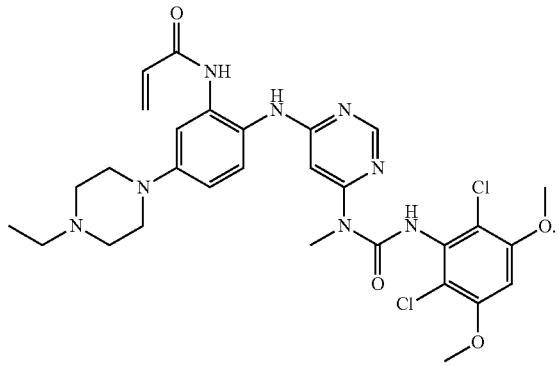

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide Such methods may include one or more of the steps of: a) providing a composition comprising a compound:

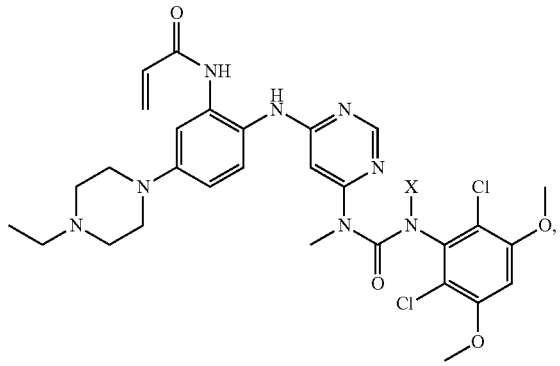

wherein X is (2-(trimethylsilyl)ethoxy)methyl, in a solvent;

b) adding an acid to said composition at such rate as to maintain a temperature of the composition at ≤50° C. (e.g., ≤30, 20, or 15° C.);

c) allowing the composition formed in step b) to warm (e.g., to room temperature); and then d) adding the composition to saturated ammonium hydroxide solution (e.g., cold, such as 0-5° C.) at such a rate as to maintain a temperature of the composition at ≤25° C.; and then e) extracting the composition with a mixture of immiscible solvents (e.g., dichloromethane/methanol) to form an organic phase; and f) adding a suitable solvent to the organic phase,
to thereby form said crystalline free base form of the compound.

A further purpose is a method of treating hepatocellular carcinoma in a subject in need thereof comprising administering to said subject a treatment effective amount of a crystalline form compound as described herein. In some embodiments, hepatocellular carcinoma has altered FGFR4 and/or FGF19 status (e.g., increased expression of FGFR4 and/or FGF19).

A further purpose is a method of treating hepatocellular carcinoma in a subject in need thereof, comprising: detecting an altered FGFR4 and/or FGF19 status (e.g., increased expression of FGFR4 and/or FGF19) in a biological sample containing cells of said hepatocellular carcinoma, and if said hepatocellular carcinoma has said altered FGFR4 and/or FGF19 status, administering a crystalline form compound as described herein to said subject in a treatment-effective amount.

A further purpose is the use of a crystalline form compound as described herein in a method of treatment of hepatocellular carcinoma.

A further purpose is the use of a crystalline form compound as described herein in the preparation of a medicament for the treatment of hepatocellular carcinoma.

DETAILED DESCRIPTION OF EMBODIMENTS

Provided herein are crystalline forms of the compound:

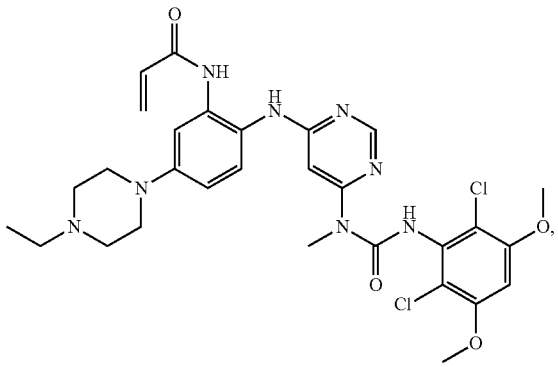

N-(2-((6-(3-(2,6-dichloro-3,5-dimethoxyphenyl)-
1-methylureido)pyrimidin-4-yl)amino)-5-(4-
ethylpiperazin-1-yl)phenyl)acrylamide which is useful as a selective FGFR4 inhibitor.

Figure 5:
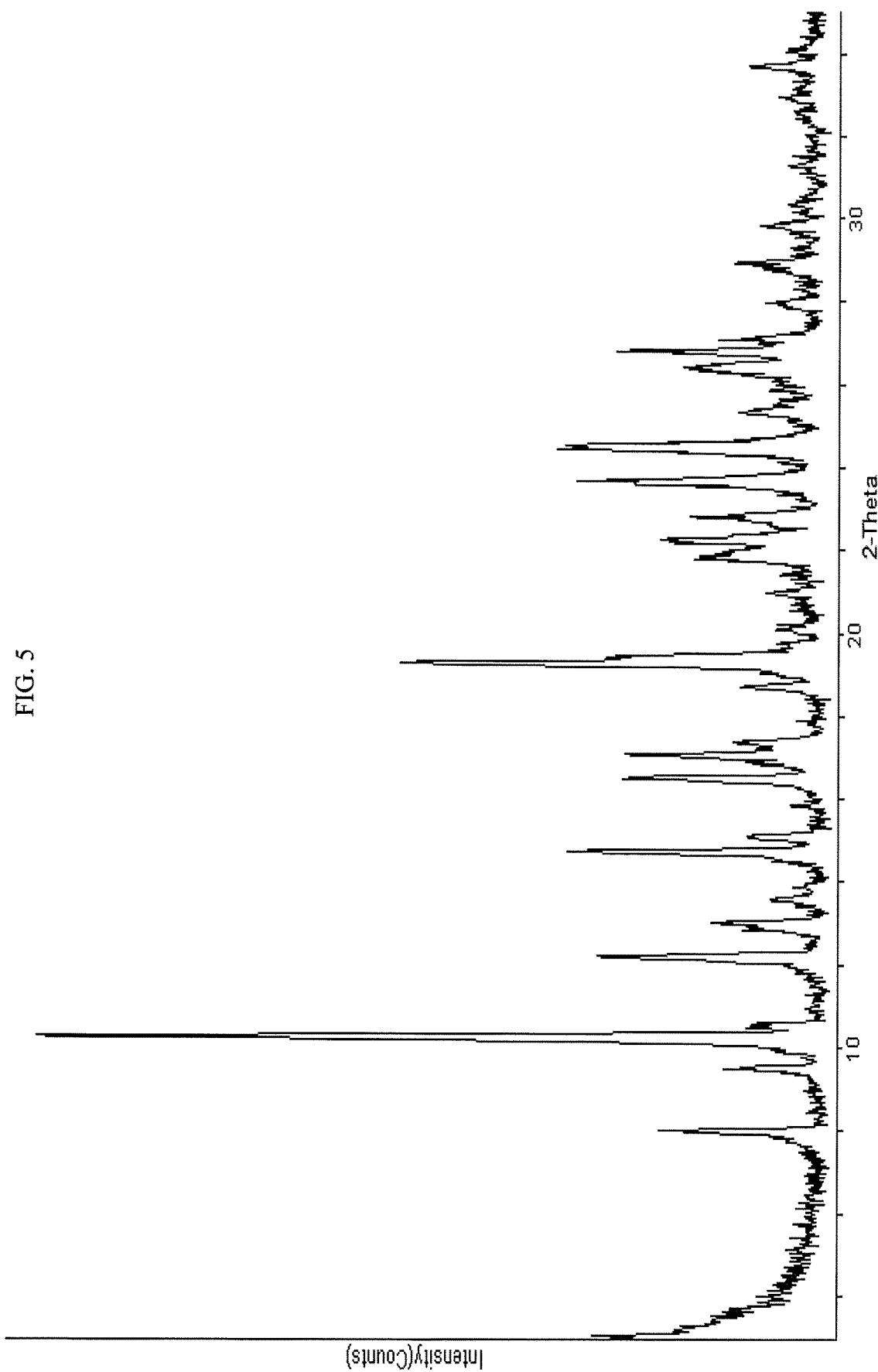
FIG. 5 presents a PXRD spectrum obtained from crystalline free base form of Compound 108.

In some embodiments, the crystalline compound is the free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide. An embodiment of the crystalline free base form gives peaks in a powder X-ray diffraction (PXRD) spectra at one, two, three, four, five, six or more of the following value ranges of 2θ°: 7.8-8.2; 10.1-10.5; 14.6-15.0; 16.3-16.7; 16.9-17.3; and 21.6-22.0. For example the crystalline free base form compound may exhibit at least one, two, three, four, five or six values selected from the group consisting of 2θ° (±0.2°): 8.0, 10.3, 14.8, 16.5 17.1 and 21.8. In some embodiments, the crystalline free base compound is characterized by a PXRD pattern substantially as shown in FIG. 5. In some embodiments the crystalline free base form of the compound gives peaks in powder X-ray diffraction spectra at the following ranges of 2θ° (±0.2): at least 10.3, 8.0 and 9.5; at least 10.3, 8.0, 9.5, 14.8, 16.5, and 17.1; or at least 10.3, 8.0, 9.5, 14.8, 16.5, 17.1, 19.3, 21.8, 23.7, and 24.5.

Figure 7:
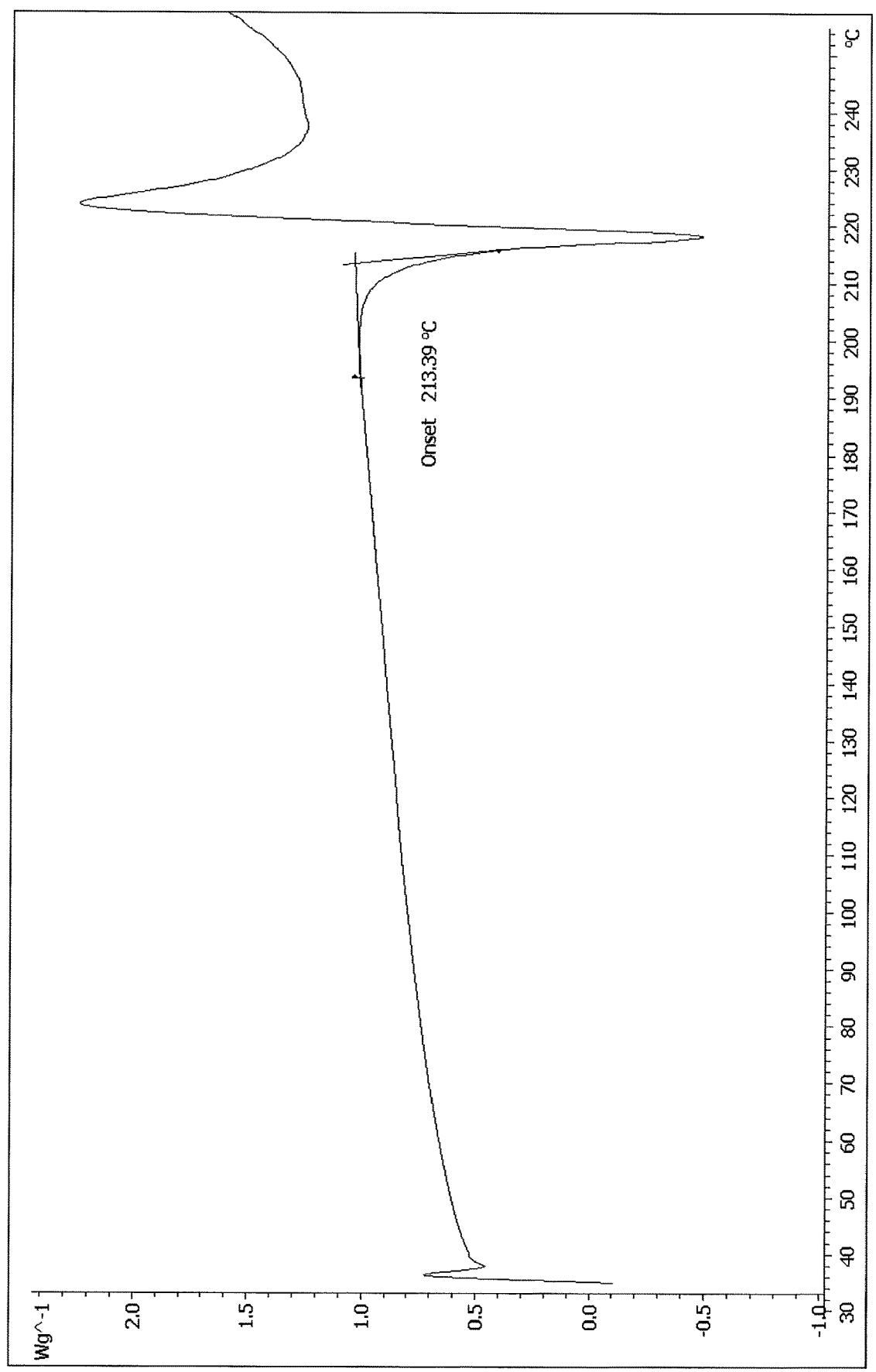
FIG. 7 presents a DSC curve for crystalline free base form of Compound 108.

In some embodiments, the crystalline free base form is characterized by a differential scanning calorimetry (DSC) curve substantially the same as shown in FIG. 7.

Figure 13:
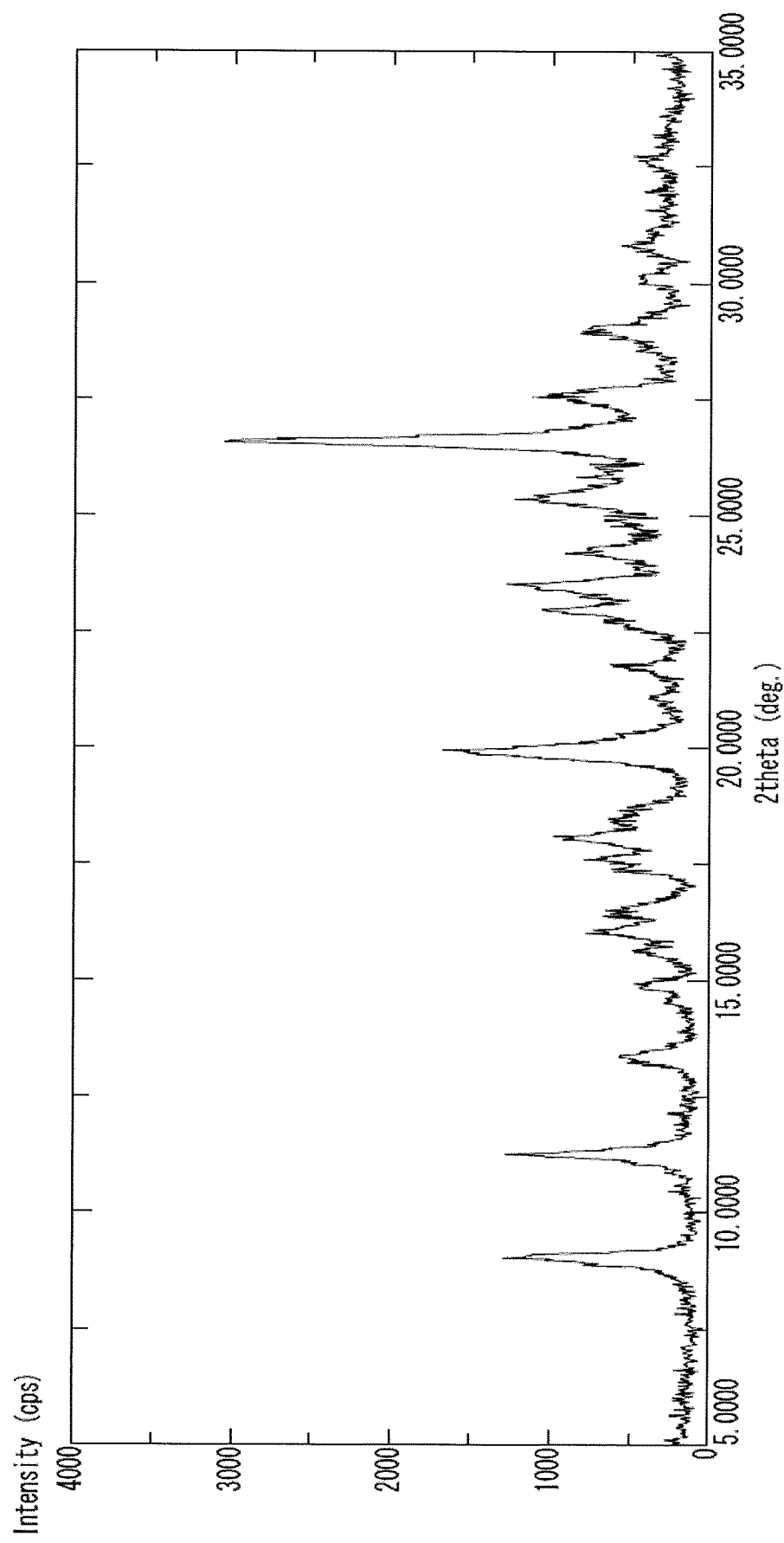
FIG. 13 presents a PXRD spectrum obtained from the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride obtained in Example 10 herein.

Some embodiments may provide a compound that is a crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride salt gives peaks in powder X-ray diffraction spectra at the following ranges of 2θ° (±0.2): at least 26.6, 19.9, and 11.3; at least 26.6, 19.9, 11.3, 9.0, 23.5, and 25.4; or at least 26.6, 19.9, 11.3, 9.0, 23.5, 25.4, 27.6, 23.0, 18.1, and 29.0. Such an embodiment may have a PXRD spectrum as shown in FIG. 13.

Figure 16:
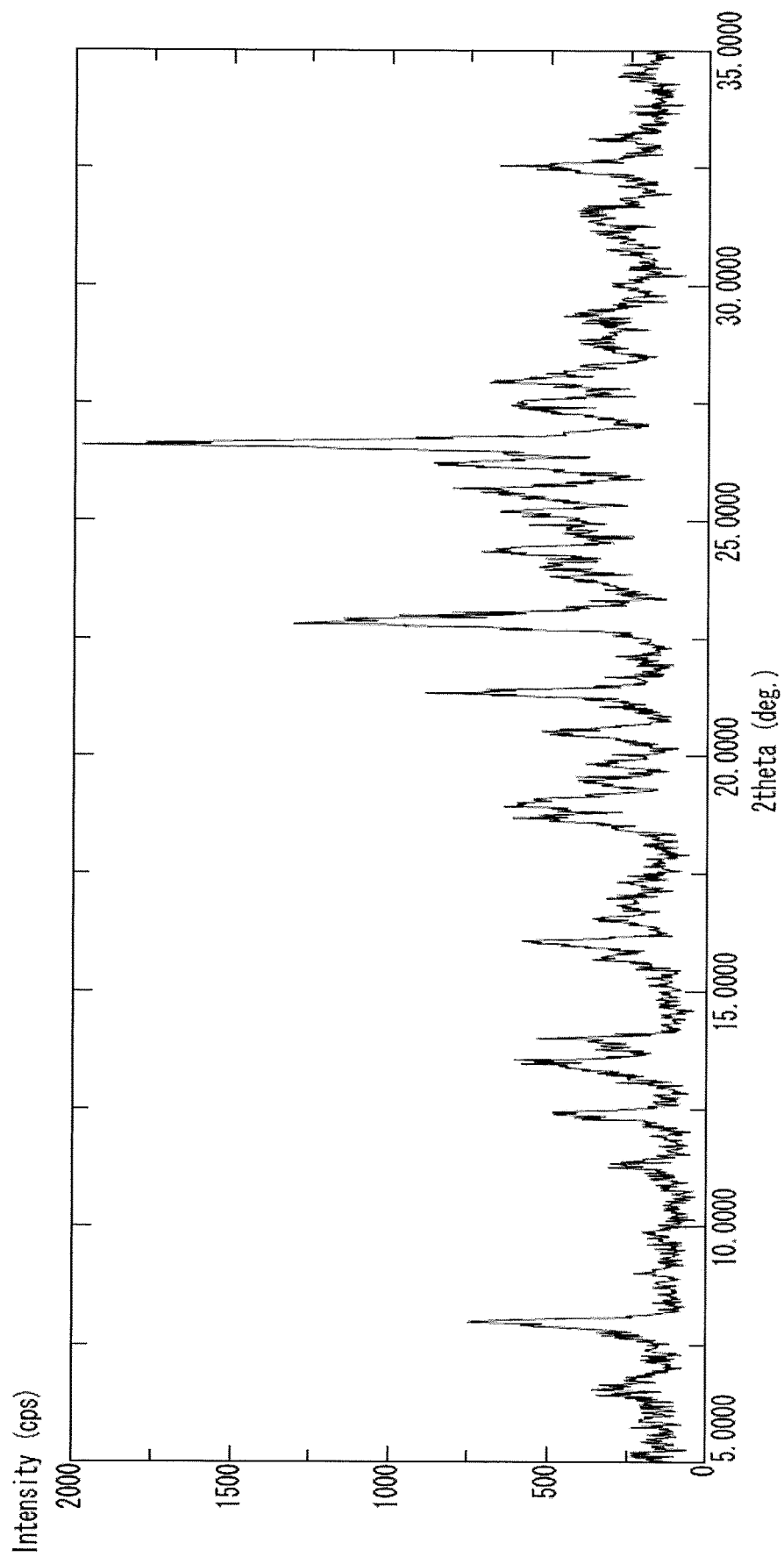
FIG. 16 presents a PXRD spectrum obtained from the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride obtained in Example 13 herein.

Some embodiments may provide a compound that is a crystalline form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride salt gives peaks in powder X-ray diffraction spectra at the following ranges of 2θ° (±0.2): at least 26.6, 22.8, and 21.3; at least 26.6, 22.8, 21.3, 8.0, 26.2, and 13.5; or at least 26.6, 22.8, 21.3, 8.0, 26.2, 13.5, 12.4, 16.1, 28.0, and 18.7. Such an embodiment may have a PXRD spectrum as shown in FIG. 16.

Figure 19:
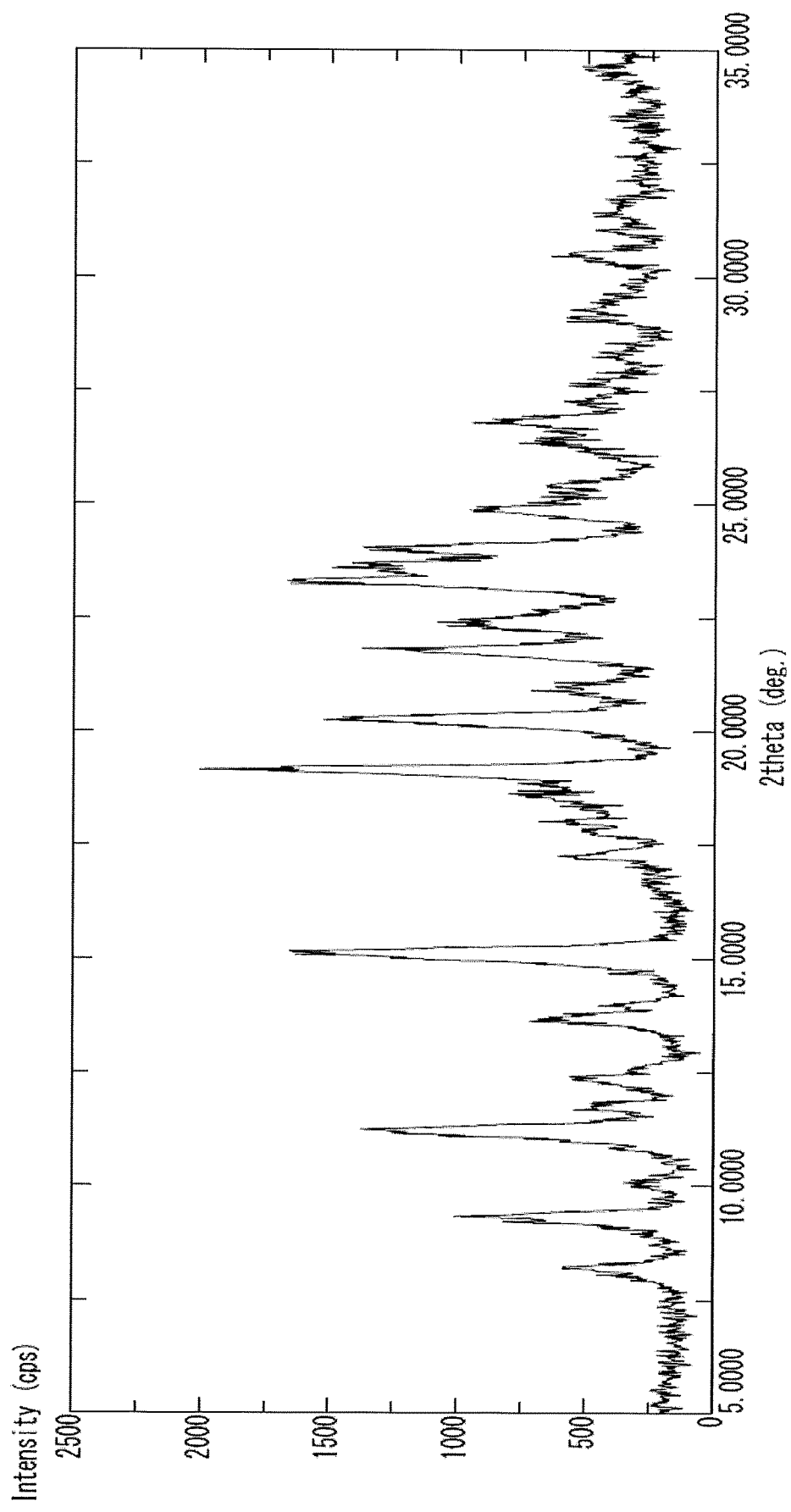
FIG. 19 presents a PXRD spectrum obtained from the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate obtained in Example 16 herein.

Embodiments may provide a compound that is a crystalline form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt. In some embodiments the crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate salt gives peaks in powder X-ray diffraction spectra at the following ranges of 2θ° (±0.2): at least 19.2, 15.1, and 23.3; at least 19.2, 15.1, 23.3, 20.3, 11.2, and 21.8; or at least 19.2, 15.1, 23.3, 20.3, 11.2, 21.8, 9.4, 22.4, 23.6, and 24.0. Such an embodiment may have a PXRD spectrum as shown in FIG. 19.

Figure 6:
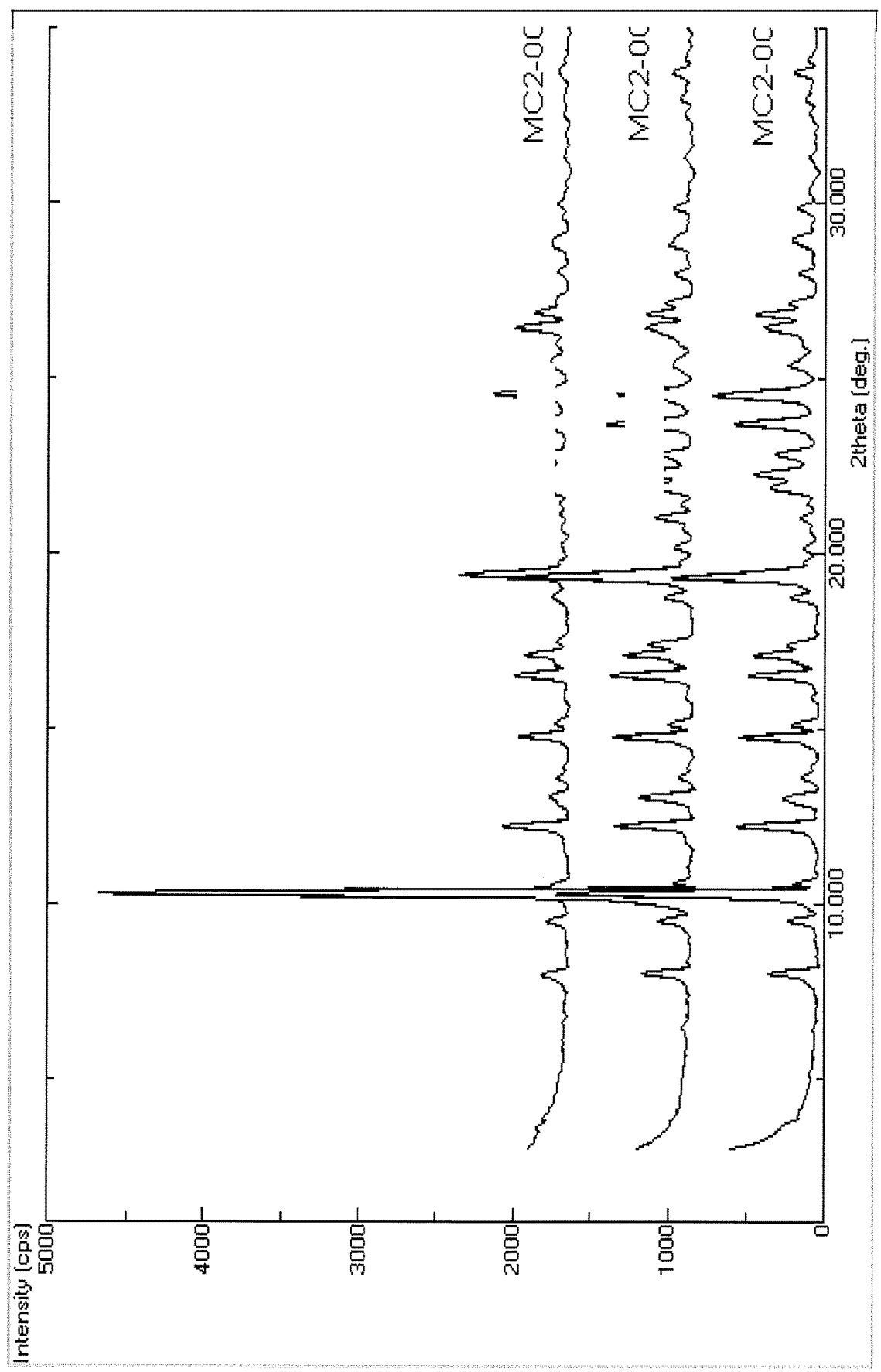
FIG. 6 presents an overlay of crystalline free base form of Compound 108 PXRD spectra from three lots.

As used herein, "substantially as shown." "substantially the same," or "substantially as indicated" with reference to data such as a spectrum means that the skilled person, when comparing such spectra obtained using the same methods of collection of the data, for example, such as shown in FIG. 6, would conclude that the spectra are similar enough to be indicative of the same crystalline free base form of the compound as taught herein.

Also provided are methods of synthesizing and crystallizing compounds as taught herein. For a crystalline free base form, methods may include one or more of the steps of: a) providing a composition comprising a compound:

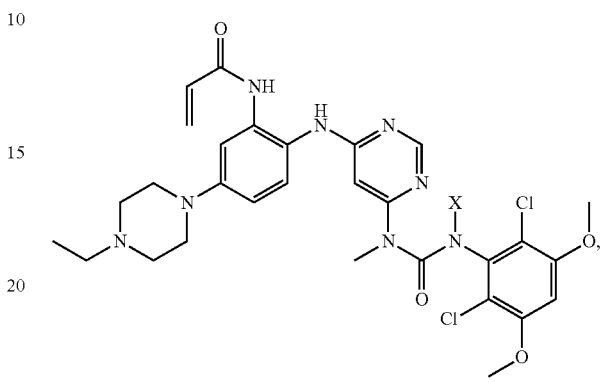

wherein X is (2-(trimethylsilyl)ethoxy)methyl, in a solvent;

b) adding an acid to said composition at such rate as to maintain a temperature of the composition ≤50° C. (e.g., ≤30, 20, or 15° C.);

c) allowing the composition formed in step b) to warm (e.g., to room temperature); and then d) adding the composition to saturated ammonium hydroxide solution (e.g., cold, such as 0-5° C.) at such a rate as to maintain a temperature of the composition ≤25° C.; and then e) extracting the composition with a mixture of immiscible solvents (e.g., dichloromethane/methanol) to form an organic phase; and f) adding a suitable solvent to the organic phase, to thereby form said crystalline free base form of the compound.

A crystalline compound as reported herein may be combined with a pharmaceutically acceptable carrier to provide pharmaceutical formulations thereof. The particular choice of carrier and formulation will depend upon the particular route of administration for which the composition is intended. In some embodiments, the carrier is selected so as to maintain the crystalline form of the compound prior to administration.

"Pharmaceutically acceptable carrier" as used herein refers to a nontoxic carrier, adjuvant, or vehicle that does not destroy the pharmacological activity of the compound with which it is formulated. In some embodiments, the pharmaceutically acceptable carrier is selected so as to maintain the crystalline free base form of the compound. Pharmaceutically acceptable carriers, adjuvants or vehicles may include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprise ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Subjects and Methods of Use

The crystalline form of the compound as taught herein may be used to treat hepatocellular carcinoma.

"Treatment," "treat," and "treating" refer to reversing, alleviating, delaying the onset of, inhibiting the progress of, or otherwise ameliorating a disease or disorder as described herein. In some embodiments, treatment may be administered after one or more symptoms have developed.

In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

"Patient" or "subject", as used herein, means an animal subject, preferably a mammalian subject, and particularly human subjects (including both male and female subjects, and including neonatal, infant, juvenile, adolescent, adult and geriatric subjects). Subjects may also include other mammalian subjects (e.g., dog, cat, horse, cow, sheep, goat, monkey, bird, etc.), for laboratory or veterinary purposes.

In some embodiments, treatment is provided to a subject having hepatocellular carcinoma with altered FGFR4 and/or FGF19 (fibroblast growth factor 19) status.

In some embodiments, treatment may include or be performed in conjunction with analyzing (e.g., measuring or assaying for) FGFR4 and/or FGF19 status in a biological sample containing cells of said hepatocellular carcinoma, and if said hepatocellular carcinoma exhibits an FGFR4 and/or FGF19 alteration, treating a subject with a treatment effective amount of an active agent as described herein.

"Altered status" as used herein with reference to FGFR4 and/or FGF19 includes an increased expression thereof (e.g., increased levels of the mRNA or increased levels of the protein), increased copy number in the genome, and/or increased activity of the encoded protein as a result of mutation, etc., as compared to a corresponding non-cancerous tissue. In some embodiments, altered status of FGFR4 and/or FGF19 includes gene and/or encoded protein mutations that result in an increase in activity or are otherwise associated with a more aggressive form of hepatocellular carcinoma.

"Expression" of FGFR4 and/or FGF19 means that a gene encoding the same is transcribed, and preferably, translated. Typically, expression of a coding region will result in production of the encoded polypeptide.

The FGFR4 and FGF19 proteins are known, and their altered status and/or expression may be measured using techniques standard in the art, e.g., genomic analysis of mutations or copy number aberrations such as by nucleic acid amplification, sequencing analysis, and/or hybridization-based techniques, RNA expression analysis such as northern blot or qRT-PCR, western blot or other immunoblot or immunoassay, fluorescent activated cell sorting (FACS), etc.

In order that the invention described herein may be more fully understood, the following examples are set forth. It should be understood that these examples are for illustrative purposes only and are not to be construed as limiting.

EXAMPLES

Example 1: Procedures for the Synthesis of (Compound 108)

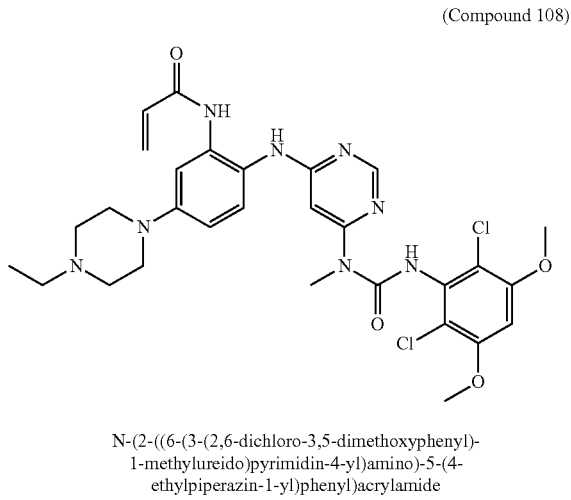 [SMILES: C=CC(=O)Nc1cc(N2CCN(CC)CC2)ccc1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide General:

Microwave heating was done using a Biotage Emrys Liberator or Initiator microwave. Column chromatography was carried out using an Isco Rf200d. Solvent removal was carried out using either a Büchi rotary evaporator or a Genevac centrifugal evaporator. Preparative LC/MS was conducted using a Waters autopurifier and 19×100 mm XTerra 5 micron MS C18 column under acidic mobile phase conditions. NMR spectra were recorded using a Varian 400 MHz spectrometer. Analytical mass spectra (MS) results were obtained using a Waters Acquity UPLC equipped with a single quadrapole MS detector (Waters SQD).

Preparative HPLC Conditions for Purification
  Chromatography Conditions:
  Instrument: Waters 2767-SQD Mass trigger Prep System
  Column: Waters Xbridge C18 150 mm*19 mm*5 μm
  Detector: VWD SQD
  Flow Rate: 15 mL/min
  Gradient Time:

| Time(min) | B % |
|---|---|
| 0 | 5 |
| 7.5 | 70 |
| 8 | 95 |
| 11 | 95 |

Representative Mobile Phase:
1)
Mobile Phase: A: 0.1% TFA in water
Mobile Phase: B: ACN
2)
Mobile Phase: A: 0.10% $NH_4HCO_3$ in water
Mobile Phase: B: ACN
3)
Mobile Phase: A: 0.10% $NH_4OAc$ in water
Mobile Phase: B: ACN
4)
Mobile Phase: A: 0.10% $NH_4OH$ in water
Mobile Phase: B: ACN Definitions:
  The following abbreviations have the indicated meanings:
  ACN: Acetonitrile
  $Boc_2O$: Di-tert-butyl dicarbonate
  Brettphos: 2-(Dicyclohexylphosphino)-3,6-dimethoxy-2',4',6'-triisopropyl-1,1'-biphenyl
  tBuONa: Sodium tert-butoxide
  $CH_3I$: Iodomethane
  $Cs_2CO_3$: Cesium carbonate
  DCC: N,N'-dicyclohexylcarbodiimide
  DCM: Dichloromethane
  DIEA: N,N-diisopropylethylamine
  DIPEA: N,N-diisopropylethylamine
  DMAP: 4-(Dimethylamino)pyridine
  DME: Dimethyl ether
  DMF: Dimethylformamide
  DMSO: Dimethyl sulfoxide
  EGTA: Ethylene glycol tetraacetic acid
  ESI-MS: Electrospray ionization-mass spectrometry
  EtOH: Ethanol
  HATU: 1-[Bis(dimethylamino)methylene]-1H-1,2,3-trizolo[4,5-b]pyridinium 3-oxid hexafluorophosphate
  $H_2SO_4$: Sulfuric acid
  iPrOH: Isopropanol
  $K_2CO_3$: Potassium carbonate
  KHMDS: Potassium bis(trimethylsilyl)amide
  KOH: Potassium hydroxide
  LCMS: Liquid chromatography-mass spectrometry
  MeOH: Methanol
  MsCl: Methansulfonyl chloride
  $NaBH_3CN$: Sodium cyanoborohydride
  $NaBH(OAc)_3$: Sodium triacetoxyborohydride
  $NH_4Cl$: Ammonium chloride
  $NH_4HCO_3$: Ammonium bicarbonate
  NaI: Sodium iodide
  $NaNO_3$: Sodium nitrate
  NaOAc: Sodium acetate
  MTBE: Methyl tert-butyl ether
  nBuOH: n-Butanol
  prep-HPLC: Preparative high-performance liquid chromatography
  prep-TLC: Preparative thin layer chromatography
  TBAF: Tetrabutylammonium fluoride
  TBDMS-CL: tert-Butyldimethylsilyl chloride
  TBSCl: tert-Butyldimethylsilyl chloride
  TBSOTf: tert-Butyldimethylsilyl trifluoromethanesulfonate
  TEA: Triethylamine
  TESCl: Chlorotriethylsilane
  TFA: Trifluoroacetic acid
  THF: Tetrahydrofuran
  $Ti(O^iPr)_4$: Titanium isopropoxide
  TLC: Thin-layer chromatography
  PPTS: Pyridinium p-toluenesulfonate
  PE: Petroleum ether
  PEG: Poly(ethylene glycol)
  $PtO_2$: platinum dioxide
  EtOAc: Ethyl acetate
  Pd/C: Palladium (0) on carbon
  $Pd_2(dba)_3$: Tris(dibenzylideneacetone) dipalladium(0)
  $Pd(dppf)_2Cl_2$: [1,1'-Bis(diphenylphosphino)ferrocene]dichloropalladium(II)
  Ruphos: 2-Dicyclohexylphosphino-2',6'-diisopropoxybiphenyl
  Xantphos: 4,5-Bis(diphenylphosphino)-9,9-dimethylxanthene As used in the specification and claims, the singular forms "a," "an," and "the" include plural references unless the content dictates otherwise. Thus, for example, reference to "an HCl salt" makes reference to monohydrochloride salts, dihydrochloride salts, 1.5 hydrochloride salts, and other stoichiometric and nonstoichiometric hydrochloride salts.

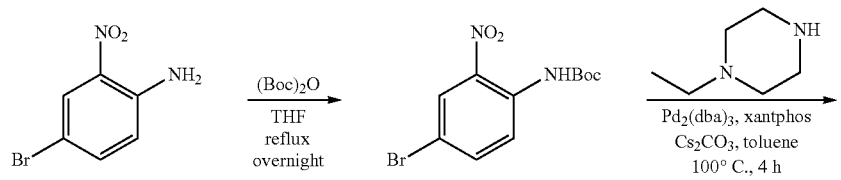
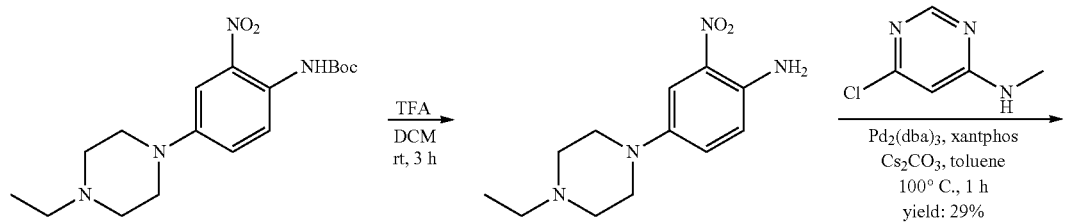
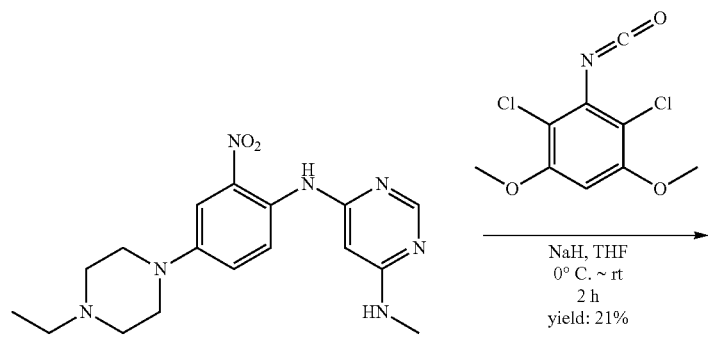
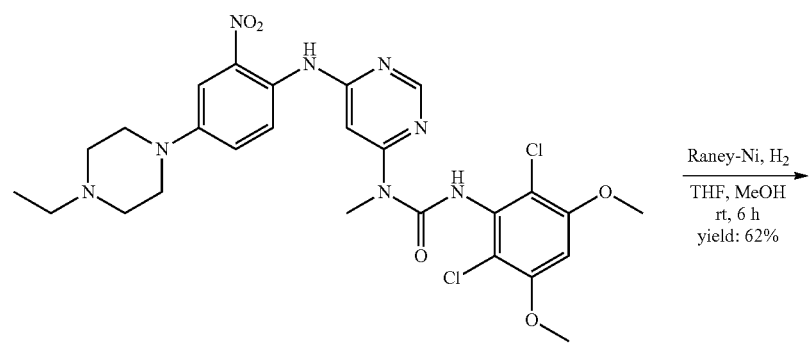
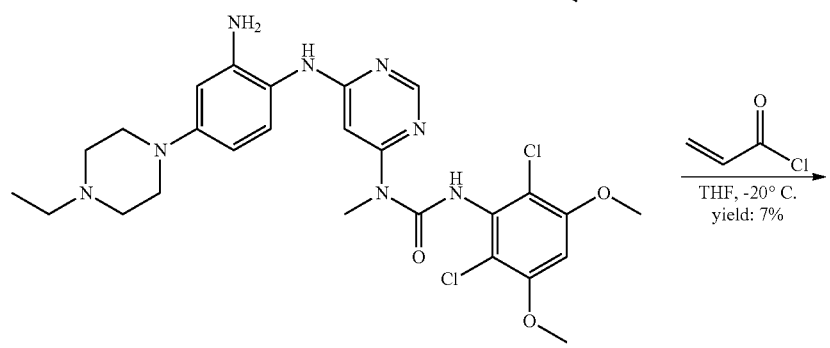

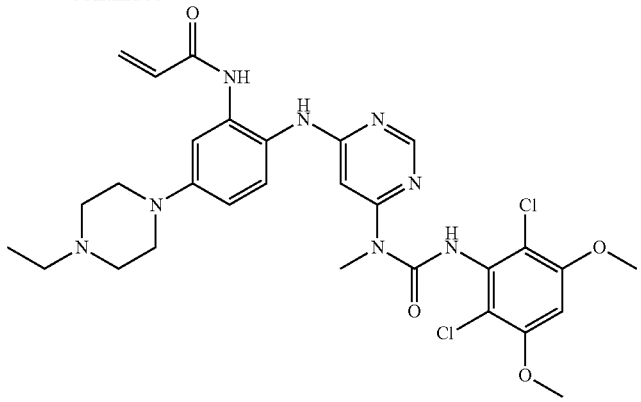 [SMILES: C=CC(=O)Nc1cc(N2CCN(CC)CC2)ccc1Nc1cc(N(C)C(=O)Nc2c(Cl)c(OC)cc(OC)c2Cl)ncn1]

N-[2-{6-[3-(2,6-dichloro-3,5-dimethoxy-phenyl)-1-methyl-ureido]-pyrimidin-4-ylamino}-5-(4-ethyl-piperazin-1-yl)-phenyl]-acrylamidemethane

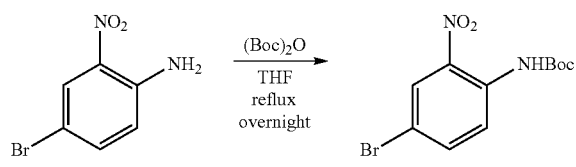 [SMILES: "(Boc)2O" ; Nc1ccc(Br)cc1[N+](=O)[O-] ; CC(C)(C)OC(=O)Nc1ccc(Br)cc1[N+](=O)[O-]]

a. tert-Butyl 4-bromo-2-nitrophenylcarbamate

A mixture of 4-bromo-2-nitroaniline (4 g, 18.4 mmol), (Boc)$_2$O (4.4 g, 20.24 mmol) in THF (50 mL) was heated under reflux overnight. The mixture was concentrated and the residue was purified by flash chromatography on silica eluting with PE:EtOAc=20:1 to obtain the title compound (5.4 g, yield: 93%). MS (ESI): 317, 319 [M+H]$^+$.

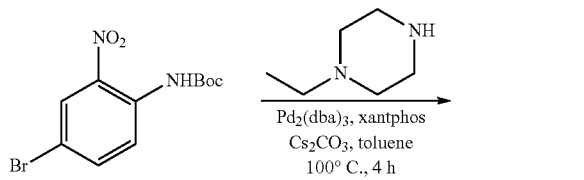

b. tert-Butyl 4-(4-ethylpiperazin-1-yl)-2-nitrophenylcarbamate

A degassed mixture of tert-butyl 4-bromo-2-nitrophenylcarbamate (5.4 g, 17 mmol), 1-ethylpiperazine (2.91 g, 25.5 mmol), Pd$_2$(dba)$_3$ (2.1 g, 3.4 mmol), xantphos (3.92 g, 6.8 mmol) and Cs$_2$CO$_3$ (11.1 g, 34 mmol) in toluene (85 mL) was heated at 100° C. for 4 hours. The reaction was concentrated, and the residue was purified by flash chromatography on silica eluting with MeOH:DCM=1:50-1:20 to obtain the title compound (3.3 g, yield: 55%). MS (ESI): 351 [M+H]$^+$.

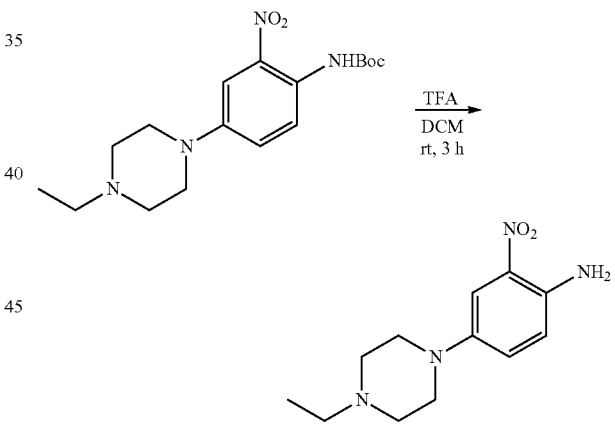

c. 4-(4-Ethylpiperazin-1-yl)-2-nitroaniline

To a solution of tert-butyl 4-(4-ethylpiperazin-1-yl)-2-nitrophenylcarbamate (3.3 g, 9.43 mmol) in DCM (50 mL) was added TFA (20 mL) at 0° C., the resulting mixture was stirred for 3 hours at rt. After removal of all volatiles in vacuo, the residue was re-dissolved in DCM, neutralized with saturated aqueous K$_2$CO$_3$ and extracted with DCM. The combined extracts were concentrated to obtain the title compound (2.1 g, yield: 90%), which was used directly in the next step. $^1$H NMR (400 MHz, DMSO-d6) δ 1.02 (t, 3H), 2.36 (q, 2H), 2.47-2.49 (m, 4H) 2.97-3.00 (m, 4H), 6.97 (d, 1H), 7.20 (s, 2H), 7.25 (s, 1H), 7.34 (dd, 1H); MS (ESI): 251 [M+H]$^+$.

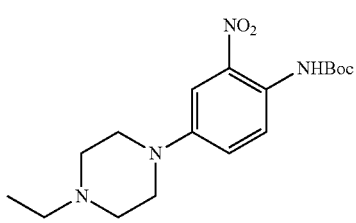

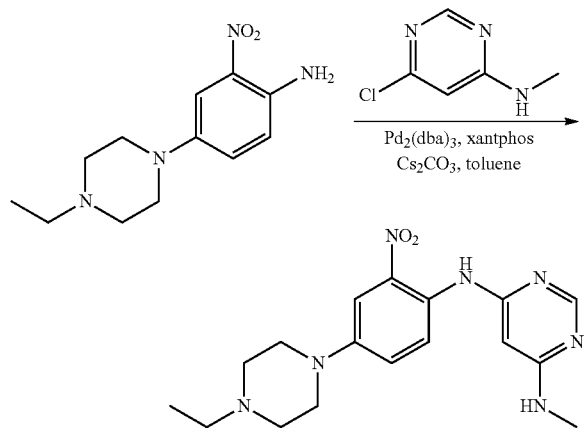

d. N⁴-(4-(4-ethylpiperazin-1-yl)-2-nitrophenyl)-N⁶-methylpyrimidine-4,6-diamine A degassed mixture of 4-(4-ethylpiperazin-1-yl)-2-nitroaniline (2.1 g, 8.4 mmol), 6-chloro-N-methylpyrimidin-4-amine (Procedure 2A, step e; 1.2 g, 8.4 mmol), Pd₂(dba)₃ (1.54 g, 1.68 mmol), xantphos (1.94 g, 3.36 mmol) and Cs₂CO₃ (5.48 g, 16.8 mmol) in toluene (45 mL) was heated at 100° C. for 1 hour. The reaction was concentrated, and the residue was purified by flash chromatography on silica eluting with MeOH:DCM=1:40-1:20 to obtain the title compound (870 mg, yield: 29%). MS (ESI): 358 [M+H]⁺.

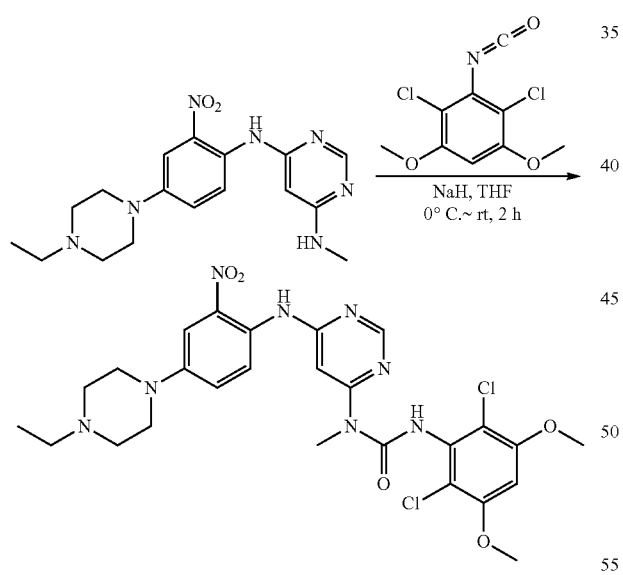

e. 3-(2,6-Dichloro-3,5-dimethoxyphenyl)-1-(6-(4-(4-ethylpiperazin-1-yl)-2-nitrophenylamino)pyrimidin-4-yl)-1-methylurea To a solution of N⁴-(4-(4-ethylpiperazin-1-yl)-2-nitrophenyl)-N⁶-methylpyrimidine-4,6-diamine (870 mg, 2.44 mmol) in THF (15 mL) was added NaH (60%, 200 mg, 5 mmol) at 0° C., and the mixture was stirred for 30 minutes at room temperature. A solution of 2,4-dichloro-3-isocyanato-1,5-dimethoxy-benzene (Procedure 2A, steps a-d; 908 mg, 3.66 mmol) in THF was added dropwise at 0° C. The resulting mixture was stirred at room temperature for 2 hours. Saturated aqueous NH₄Cl solution (2 mL) was added to quench the reaction. The mixture was concentrated and extracted with DCM. The combined extracts were washed with brine, dried over anhydrous Na₂SO₄, and concentrated to give the crude product, which was purified by flash chromatography on silica to obtain the title compound (330 mg, yield: 21%) as a red oil. ¹H NMR (400 MHz, CDCl₃) δ 1.44 (t, 3H), 3.01 (t, 2H), 3.21 (q, 2H), 3.41-3.49 (m, 5H), 3.73-3.80 (m, 4H), 3.92 (s, 6H), 6.27 (s, 1H), 6.55 (s, 1H), 7.25 (d, 1H), 7.69 (s, 1H), 8.32 (d, 1H), 8.52 (s, 1H), 10.28 (br s, 1H), 12.05 (br s, 1H); MS (ESI): 605 [M+H]⁺.

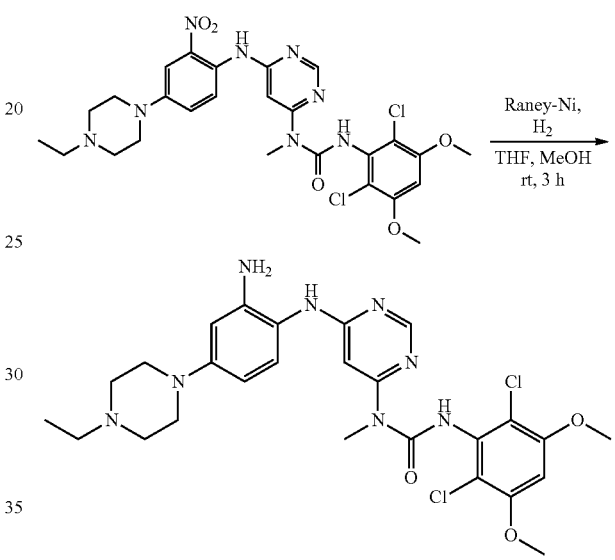

f. 1-(6-(2-Amino-4-(4-ethylpiperazin-1-yl)phenylamino)pyrimidin-4-yl)-3-(2,6-dichloro-3,5-dimethoxyphenyl)-1-methylurea To a solution of 3-(2,6-dichloro-3,5-dimethoxyphenyl)-1-(6-(4-(4-ethylpiperazin-1-yl)-2-nitrophenylamino)pyrimidin-4-yl)-1-methylurea (330 mg, 0.546 mmol) in THF (20 mL) and MeOH (20 mL) was added Raney-Ni (suspension in water) at room temperature, the resulting mixture was stirred for 3 hours under hydrogen atmosphere (1 atm). The reaction was filtered and concentrated. The residue was washed twice with MeOH to obtain the title compound (280 mg, purity: 90%), which was used directly in the next step. MS (ESI): 575 [M+H]⁺.

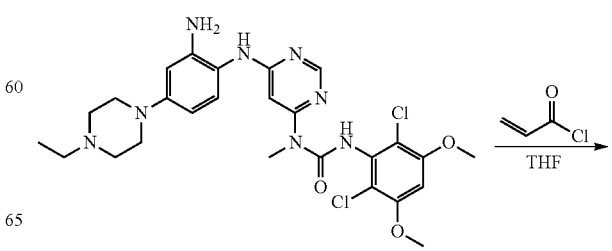

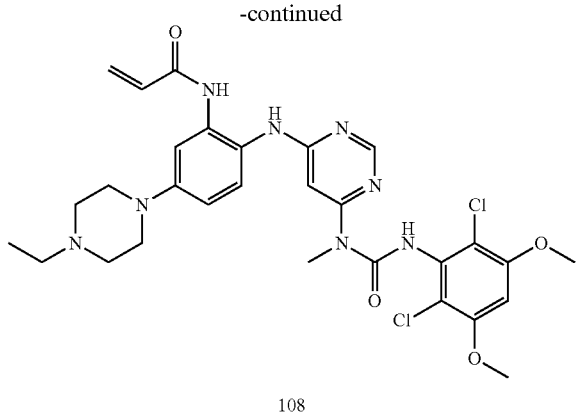

108 g. N-(2-(6-(3-(2,6-Dichloro-3,5-dimethoxyphenyl)-1-methylureido)pyrimidin-4-ylamino)-5-(4-ethylpiperazin-1-yl)phenyl)acrylamide To a solution of 1-(6-(2-amino-4-(4-ethylpiperazin-1-yl)phenylamino)pyrimidin-4-yl)-3-(2,6-dichloro-3,5-dimethoxyphenyl)-1-methylurea (280 mg, purity: 90%, 0.44 mmol) in THF (30 mL) was added a solution of acryloyl chloride in THF (20 mg/mL, 2 mL, 0.44 mmol) at −10° C., and the resulting mixture was stirred for 1 hour at this temperature. MeOH (1 mL) was added to quench the reaction. The mixture was concentrated and the residue was purified by prep-HPLC and prep-TLC to obtain the title compound 108 (20 mg, yield: 7%). $^1$H NMR (400 MHz, CDCl$_3$) δ 1.31 (t, 3H), 2.65 (q, 2H), 2.62-2.68 (m, 4H), 3.27 (s, 3H), 3.36-3.38 (m, 4H), 3.91 (s, 6H), 5.76 (d, 1H), 5.90 (s, 1H), 6.24 (dd, 1H), 6.41 (d, 1H), 6.52 (s, 1H), 6.74 (dd, 1H), 7.07 (br s, 1H), 7.23 (d, 1H), 7.72 (br s, 1H), 7.98 (br s, 1H), 8.37 (s, 1H), 12.52 (s, 1H); MS (ESI): 629 [M+H]$^+$.

Example 2: Assays of Biological Activity

Assay of Binding to FGFR4.

Purified, recombinant FGFR4 was pre-incubated with 10 μM compound overnight at 4° C., or for 1 hour at room temperature. Following pre-incubation, FGFR4 was concentrated and buffer exchanged on an OPTI-TRAP protein concentrating and desalting C4 column (Optimize Technologies). Protein was eluted in acetonitrile containing 0.1% formic acid and run by direct injection on a Thermo Scientific Q Exactive™ LCMS to identify modified, intact FGFR4.

Results provided below in Table 1 confirm covalent adduct formation of the tested compound with the peptides by correspondence of the expected mass of the peptide-ligand adduct with the mass observed.

TABLE 1

| Compound # | Expected mass [Da] | Observed mass [Da] |
|---|---|---|
| 108 | 35948.0 | 35948.1 |

IC$_{50}$ Profiling of Kinase Activity Inhibition.

Compounds were profiled for FGFR inhibition activity at Reaction Biology Corporation (Malvern, Pa.) with their Kinase HotSpot$^{SM}$ assay. See, Anastassiadis et al., 2011, Comprehensive assay of kinase catalytic activity reveals features of kinase inhibitor selectivity. Nat Biotechnol 29, 1039-1045.

Recombinant FGFR1 (2.5 nM), FGFR2 (1 nM), FGFR3 (5 nM), or FGFR4 (12 nM) (Invitrogen™) was prepared as a mixture with substrate KKKSPGEYVNIEFG (SEQ ID NO:1) (20 μM, FGFR1 substrate); and Poly [E,Y] 4:1 (0.2 mg/ml, FGFR2,3,4 substrate)] in kinase reaction buffer (20 mM HEPES-HCl, pH 7.5, 10 mM MgCl$_2$, 2 mM MnCl$_2$, 1 mM EGTA, 0.02% Brij35, 0.1 mM Na$_3$VO$_4$, 0.02 mg/ml BSA, 2 mM DTT, and 1% DMSO). Compound was added to the enzyme/substrate mixture using acoustic technology (Labcyte® Echo 550, Sunnyvale, Calif.) (see, Olechno et al., 2006, Improving IC$_{50}$ results with acoustic droplet ejection. JALA 11, 240-246) and pre-incubated for 0, 15, or 60 minutes at room temperature. After compound pre-incubation, a mixture of ATP (Sigma-Aldrich®) and $^{33}$P-γ-ATP (PerkinElmer) was added to a final concentration of 10 μM to initiate kinase reactions. Reactions were incubated for 120 minutes at room temperature and then spotted onto Whatman™ P81 ion exchange filter paper. Unbound phosphate was removed by extensively washing filters in 0.75% phosphoric acid. See, Anastassiadis et al., 2011, Comprehensive assay of kinase catalytic activity reveals features of kinase inhibitor selectivity. Nat Biotechnol 29, 1039-1045.

Results for FGFR4 and FGFR1 are shown in Table 2. Compound 108 showed selective inhibition of FGFR4, with a higher IC$_{50}$ for FGFR1.

TABLE 2

| Structure | Compound # | FGFR4 IC$_{50}$ (μM) | FGFR1 IC$_{50}$ (μM) |
|---|---|---|---|
| 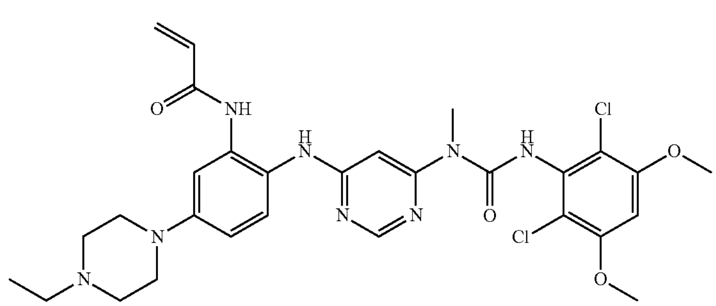 [SMILES: C=CC(=O)Nc1cc(N2CCN(CC)CC2)ccc1Nc1cc(N(C)C(=O)Nc2c(Cl)c(OC)cc(OC)c2Cl)ncn1] | 108 | <0.001 | 0.173 |

Without wishing to be bound by theory, the IC$_{50}$ activity with respect to FGFR1 is generally representative of the activity with respect to FGFR1, FGFR2, and FGFR3. See also, Dieci et al., 2013, Fibroblast Growth Factor Receptor Inhibitors as a Cancer Treatment: From a Biologic Rationale to Medical Perspectives. Cancer Discovery, F1-F16.

To confirm, the compound was also tested for FGFR2 and FGFR3 inhibition. These results shown below in Table 3 are consistent with the $IC_{50}$ activity of FGFR1 being generally representative of the activity of FGFR1, FGFR2, and FGFR3, and further demonstrates the selectivity of this FGFR4 inhibitor.

TABLE 3

| Compound # | FGFR2 $IC_{50}$ (µM) | FGFR3 $IC_{50}$ (µM) | FGFR1 $IC_{50}$ (µM) | FGFR4 $IC_{50}$ (µM) |
|---|---|---|---|---|
| 108 | 1.98 | 2.00 | 0.173 | <0.001 |

In Vivo Efficacy in Tumor Models.

Compound 108 was evaluated for its ability to inhibit tumor growth in nude mice bearing tumor xenografts from three different human hepatocellular carcinoma tumor cell lines. These cell lines are representative of cancers having an altered FGFR4 and/or FGF19 status. See Sawey et al., Cancer Cell 19(3): 347-358 (2011).

Animals:

Nude mice, ages 6-8 weeks, and weighing approximately 19-25 g, were purchased from Taconic (Taconic, Hudson, N.Y.). All animal experiments were done in accordance with protocols approved by the Institutional Animal Care and Use Committee.

Tumor Xenografts and Treatment:

$7.5 \times 10^6$ HUH7 cells (HSRRB cat. no. JCRB0403), $5 \times 10^6$ Hep3B (ATCC cat. no. HB8064), or $2.5 \times 10^6$ JHH7 cells (HSRRB cat. no. JCRB1031), each in a total volume of 100 µl, 1:1 Matrigel (Corning Inc, Corning, N.Y.), were injected subcutaneously (s.c.) into the right lateral flank. When tumors reached 150-200 mm³, the mice were randomized into treatment groups of 5-10 animals. Dosing was performed twice daily by intraperitoneal injection at the indicated dosages for 15 days using Compound 108, formulated in a vehicle of 5% DMSO (Alfa Aesar, Ward Hill, Mass.), 10% PEG300 (Sigma., St. Louis, Mo.), 8% TWEEN® 80 (Sigma, St. Louis, Mo.), 77% USP Saline at the desired concentration. Tumor volumes were collected twice weekly using the formula Volume=(length*width²)/2. Body weights were collected twice weekly, as well. All animals were observed and cared for in accordance with The Guide for Care and Use of Laboratory Animals, 8th edition (National Academies Press, Washington D.C.).

Statistical Methods:

Statistical comparisons were made at the end of the experiment using Repeated Measures Anova with Bonferroni post-test for comparisons of treatment groups, using GraphPad Prism 5. The following criteria were used to determine Progressive Disease, Stable Disease, Partial Regression, and Complete Regression. Progressive Disease is defined as three consecutive measurements increasing from best response or >120% initial tumor volume. Stable Disease is three consecutive measurements <120% and >50% of initial tumor volume, whereas three consecutive measurements <50% initial tumor volume qualifies as a Partial Regression. A Complete Regression is three consecutive measurements <30 mm³. Chi-squared test was used to compare responses between treatment groups (Microsoft Excel).

Figure 1:
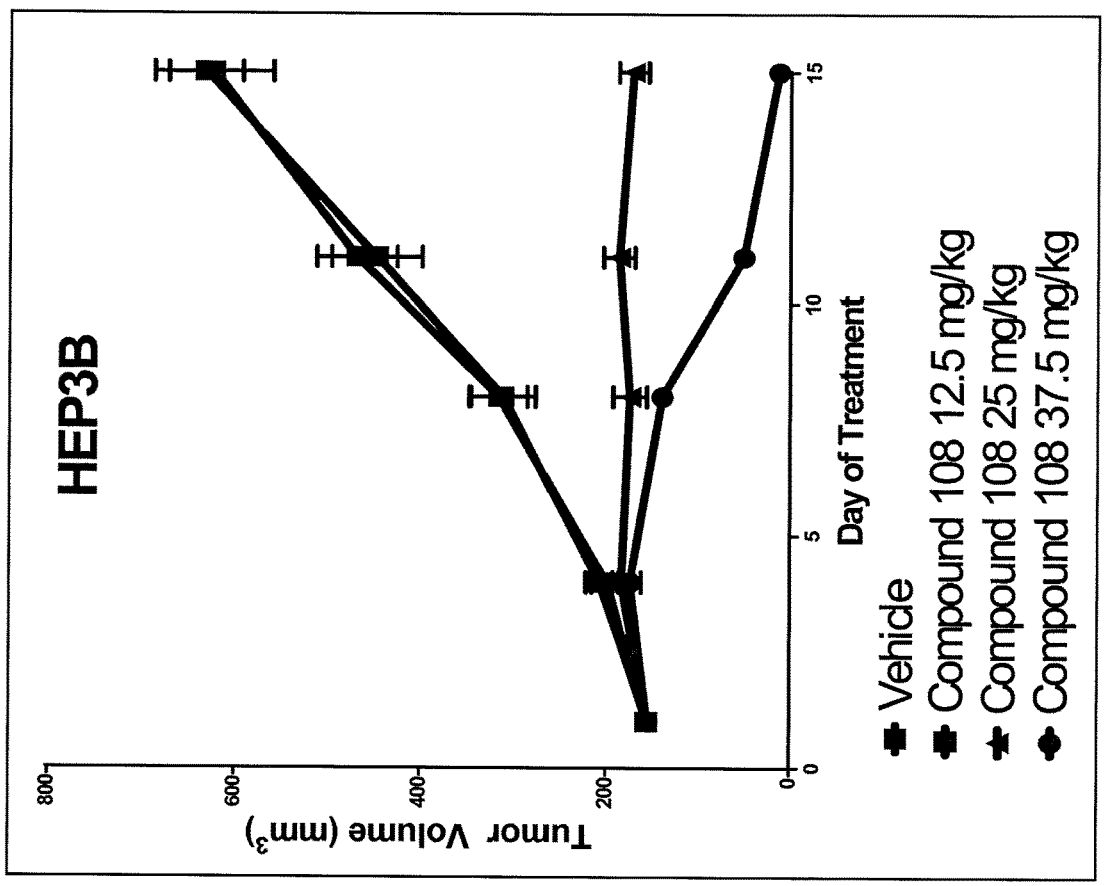
FIG. 1 presents the results of in vivo efficacy testing in hepatocellular carcinoma model using HUH7 cells. Compound 108 (25 mg/kg or 37.5 mg/kg) or Vehicle control was administered via intraperitoneal injection, and tumor volume was measured twice weekly over the course of 15 days.
Figure 2:
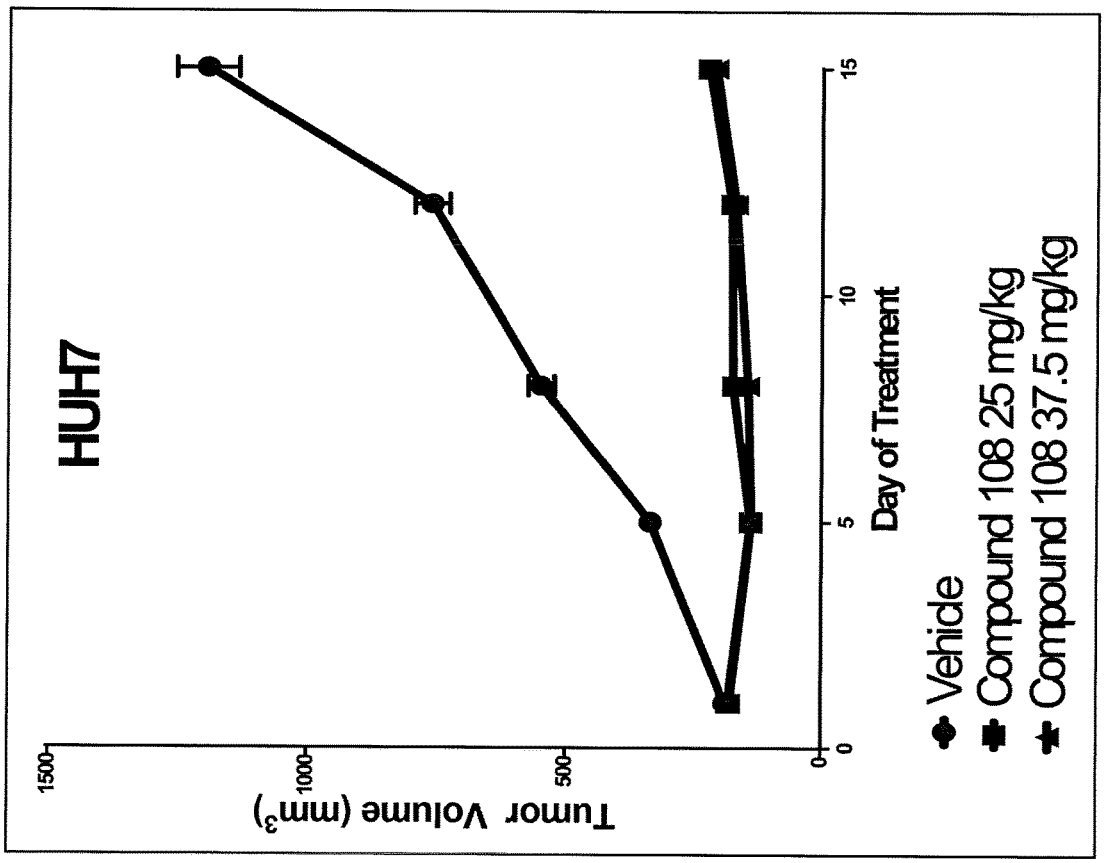
FIG. 2 presents the results of in vivo efficacy testing in hepatocellular carcinoma model using HEP3B cells. Compound 108 (12.5 mg/kg, 25 mg/kg or 37.5 mg/kg) or Vehicle control was administered via intraperitoneal injection, and tumor volume was measured twice weekly over the course of 15 days.
Figure 3:
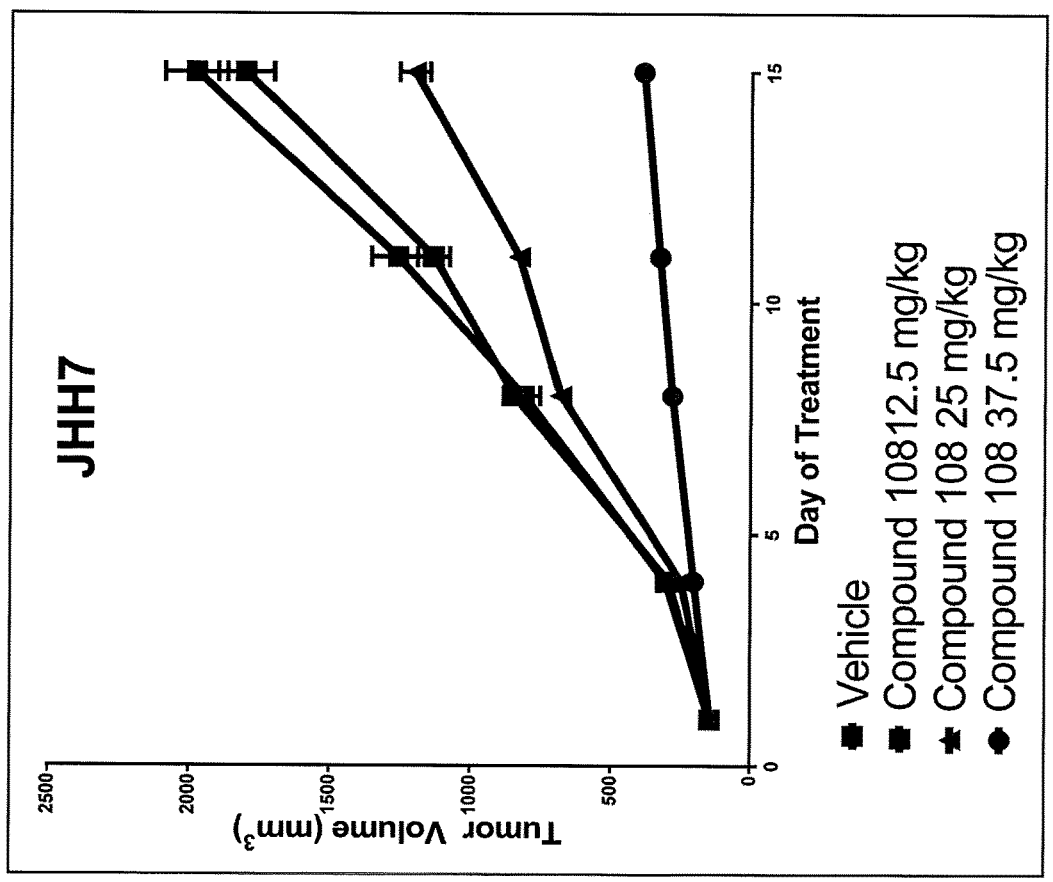
FIG. 3 presents the results of in vivo efficacy testing in hepatocellular carcinoma model using JHH7 cells. Compound 108 (12.5 mg/kg, 25 mg/kg or 37.5 mg/kg) or Vehicle control was administered via intraperitoneal injection, and tumor volume was measured twice weekly over the course of 15 days.

Results from animals bearing tumors from HUH7, HEP3B, and JHH7 cancer cells are shown in FIGS. 1-3, respectively, and are also reflected in Table 4.

TABLE 4

Inhibition of Tumor Growth in FGF19 amplified HCC xenografts

| Dose (mg/kg) | Complete Regression | Partial Regression | Stable Disease | Progressive Disease |
|---|---|---|---|---|
| HUH7 (n = 10 per group) | | | | |
| 25 | 1 | 4 | 3 | 2 |
| 37.5 | 2 | 5 | 3 | 0 |
| HEP3B (n = 5 per group) | | | | |
| 12.5 | 0 | 0 | 0 | 5 |
| 25 | 0 | 1 | 4 | 0 |
| 37.5 | 5 | 0 | 0 | 0 |
| JHH7 (n = 10 per group) | | | | |
| 12.5 | 0 | 0 | 0 | 10 |
| 25 | 0 | 0 | 0 | 10 |
| 37.5 | 0 | 0 | 0 | 10 |

These data demonstrate that compound 108 is efficacious in all models. Among the three models, HEP3B is the most sensitive, JHH7 the least sensitive and HUH7 showing intermediate sensitivity to compound 108. Although a dose response can be seen in FIG. 3 for JHH7, there was Progressive Disease in all dose levels tested.

Comparative Studies of Compound 108 with BGJ398.

Comparative studies were done with Compound 108 and the known FGFR inhibitor BJG398.

Biochemical Kinase Assay Protocol to Obtain $IC_{50}$:

Recombinant FGFR1 (2.5 nM), or FGFR4 (12 nM) was prepared as a mixture with substrate KKKSPGEYVNIEFG (SEQ ID NO:1) (20 µM, FGFR1 substrate); Poly [E,Y] 4:1 (0.2 mg/ml, FGFR2,3,4 substrate)] in kinase reaction buffer (20 mM HEPES-HCl, pH 7.5, 10 mM MgCl₂, 2 mM MnCl₂, 1 mM EGTA, 0.02%0 Brij35, 0.1 mM Na3VO4, 0.02 mg/ml BSA, 2 mM DTT, and 1% DMSO). Compound was added to the enzyme/substrate mixture using acoustic technology and pre-incubated for 0, 15, or 60 minutes at room temperature. After compound pre-incubation, $^{33}$P-γ-ATP was added at a final concentration of 10 µM to initiate kinase reactions. Reactions were incubated for 120 minutes at room temperature. Substrate phosphorylation was monitored by filter assay, as above. Results are shown in Table 5. The results reported show that compound 108 is a more potent FGFR4 inhibitor, whereas BGJ398 is a more potent FGFR1 inhibitor.

TABLE 5

Comparative Testing of Compound 108 and BGJ398 with Biochemical Kinase assay

| Kinase | Compound 108 $IC_{50}$ (nm) | BGJ398 $IC_{50}$ (nm) |
|---|---|---|
| FGFR4 | <0.2 | 13 |
| FGFR1 | 513 | 1.0 |

Cellular Viability Assay Protocol to Obtain $GI_{50}$:

Cells lines were cultured at 37° C., 5% $CO_2$ and 95% humidity. Culture media were purchased from GIBCO®, USA. For viability assay, 2000 cells/well were seeded in 96 well plates, incubated for 24h before compound treatment. Following compound addition, plates were incubate for 72h at 37° C. with 5% $CO_2$, and then measured by means of CTG assay (CellTiter-Glo® Luminescent Cell Viability Assay, Cat. No.: G7572, Promega). Results are shown in Table 6. The table shows compound 108 is more potent than BGJ398 in Hep3B cells, an FGF19 amplified line. The potency in HUH7 and JHH7, the other two FGF19 amplified lines, are comparable between compound 108 and BGJ398. HepG2 (ATCC cat. no. HB-8065), SNU398 (ATCC cat. no. CRL-2233) and SNU449 (ATCC cat. no. CRL-2234) are FGF19 non-amplified cell lines that were used as controls.

$GI_{50}$ is the concentration of test drug where $100\times(T-T0)/(C-T0)=50$. See, e.g., Monks et al., *Feasibility of a High-Flux Anticancer Drug Screen Using a Diverse Panel of Cultured Humnan Tumor Cell Lines*, J Natl Cancer Inst (1991) 83(11):757-766; Boyd et al., *Data Display and Analysis Strategies for the NCI Disease-oriented In Vitro Antitumor Drug Screen*, in CYTOTOXIC ANTICANCER DRUGS: MODELS AND CONCEPTS FOR DRUG DISCOVERY AND DEVELOPMENT, Valeriote et al., eds. (1990), pp. 11-34. The luminescence of the test well after a 72h period of exposure to test drug is T, the luminescence at time zero is T0, and the control luminescence is C. The $GI_{50}$ measures the growth inhibitory power of the test agent.

TABLE 6

Comparative Testing of Compound 108 and BGJ398 in Cellular Viability assays

| Cell Line | Compound 108 $GI_{50}$ (nm) | BGJ398 $GI_{50}$ (nm) |
|---|---|---|
| HEP3B | 18 ± 6 nm (n = 27) | 74 ± 23 nm (n = 6) |
| JHH7 | 216 ± 70 nm (n = 4) | 178 ± 30 nm (n = 2) |
| HUH7 | 408 ± 128 nm (n = 4) | 231 ± 100 nm (n = 2) |
| HEPG2 | 6506 ± 1424 nm (n = 27) | 2260 ± 1182 nm (n = 6) |
| SNU398 | >10,000 (n = 2) | not measured |
| SNU449 | >10,000 (n = 2) | not measured |

Figure 4:
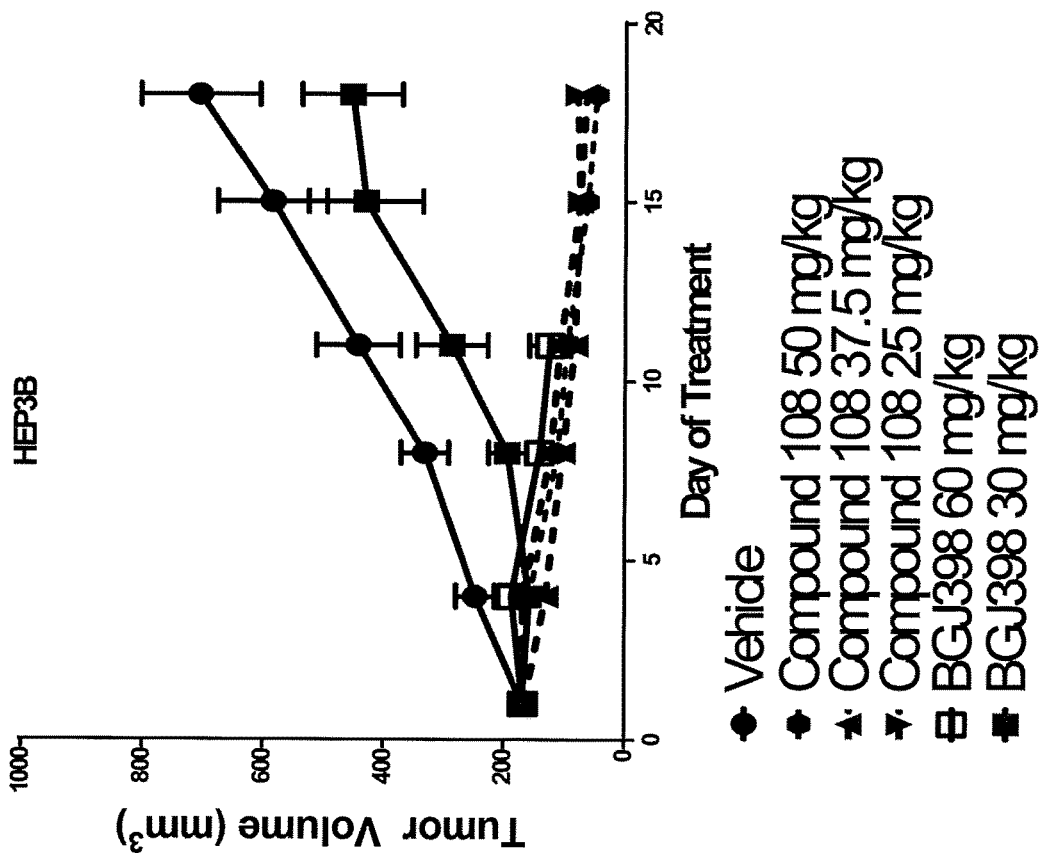
FIG. 4 presents the results of comparative in vivo efficacy testing in hepatocellular carcinoma model using HEP3B cells. Compound 108 (25 mg/kg, 37.5 mg/kg or 50 mg/kg) was administered twice daily via intraperitoneal injection, or BGJ398 (30 mg/kg or 60 mg/kg) was administered orally twice daily.

In Vivo Efficacy Comparison:

Nude mice were used for these experiments as above. $5.0\times10^6$ Hep3B cells in a total volume of 100 µl, 1:1 Matrigel (Corning Inc, Corning, N.Y.), were injected s.c. into the right lateral flank. When tumors reached 150-200 mm³ the mice were randomized into treatment groups of 5-10 animals. Treatment was then started using Compound 108, formulated in a vehicle of 5% DMSO (Alfa Aesar, Ward Hill, Mass.), 10% PEG300 (Sigma, St. Louis, Mo.), 8% TWEEN® 80 (Sigma, St. Louis, Mo.), 77% USP Saline at the desired concentration. BGJ398, formulated as a suspension in 0.5% Methylcellulose (Sigma)/0.2% TWEEN® 80, was suspended at the desired concentration. Both drugs were dosed for 18 dyas, except for one treatment group (see below). Tumor volumes were collected twice weekly using the formula Volume=(length*width²)/2. Body weights were collected twice weekly as well. All animals were observed and cared for in accordance with The Guide for Care and Use of Laboratory Animals, 8th edition (National Academies Press, Washington D.C.). The results of this comparative in vivo study are shown in FIG. 4.

The data show that compound 108 is more efficacious than BGJ398 at tolerable dosage levels. Although BGJ398 at 60 mg/kg showed efficacy comparable to compound 108, the dosing of this BGJ398 60 mg/kg group had to be terminated on Day 11 due to poor health of animals. This difference in toxicity is not due to routes of administration because the group of animals dosed orally with BGJ398 at 30 mg/kg did not exhibit poor health.

Example 3: Alternative Synthesis Methods and Crystallization of Compound 108 Synthesis of Bis(Boc)-4-Bromo-2-Nitroaniline

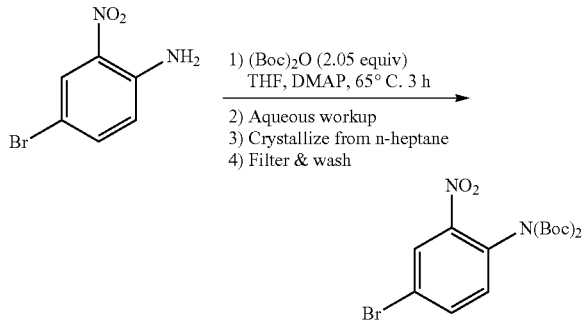

A 3-necked 5 L round bottom flask was charge with 4-bromo-3-nitroaniline (200 g, 922 mmol), Boc anhydride (412 g, 1889 mmol, 2.05 equiv), and THF (3 L). To the stirred mixture was charged DMAP (11.26 g, 92.2 mmol, 0.10 equiv). The mixture was heated to 65° C. and stirred at this temperature until the reaction was deemed complete by HPLC (≤2% 4-bromo-3-nitroaniline remaining, ca. 3.5 hours) and then cooled to room temperature. The mixture was transferred to a 12 L workup vessel, ethyl acetate was added (3 L) and the mixture was washed sequentially with with 1N HCl (1 L), saturated aqueous NaHCO₃ solution (1 L), and 10% aqueous NaCl solution (1 L). The organic layer was concentrated to a minimum stirrable volume and ethyl acetate (1 L) was added. The solution was chased twice with heptane (1.5 L), concentrated the mixture to a total volume of 1.5 L following the second chase. The resulting slurry was filtered, washed with heptane (3×200 mL), and dried under vacuum to provide the title compound (345.5 g, 90% yield) as an off-white solid.

tert-butyl (4-(4-ethylpiperazin-1-yl)-2-nitrophenyl) carbamate

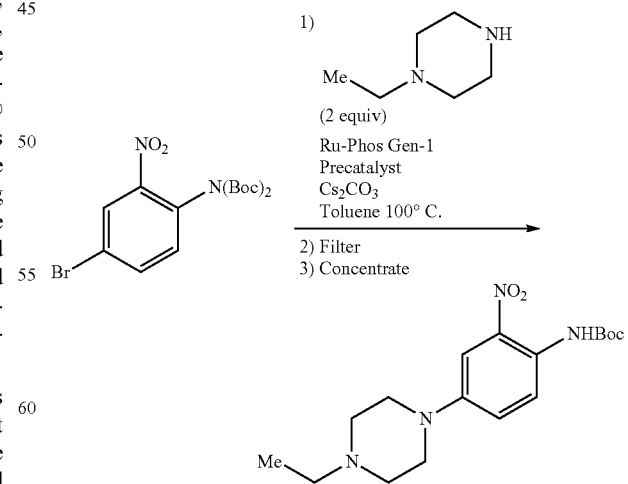

A 5 L 3-necked round bottom flask was charged with Bis(Boc)-4-bromo-2-nitroaniline (250 g, 599 mmol), cesium carbonate (234 g, 719 mmol, 1.2 equiv), and Buchwald Ru-Phos pre-catalyst (CAS #1375325-68-00, 20 g, 27.4 mmol, 0.046 equiv). To the solids was charged previously degassed toluene (1 L) and N-ethylpiperazine (156 mL, 1228 mmol, 2.05 equiv). The resulting mixture was sparged with nitrogen gas for 30 mins, then heated the mixture to 95-105° C. and stirred at this temperature until HPLC analysis showed complete reaction (ca. 6 hours). The mixture was cooled to room temperature and filtered over Celite® 545 (125 g), washing the cake with toluene (3×60 mL). The resulting solution was concentrated to afford the title compound (210 g, 100% yield) which was carried forward without further purification.

4-(4-Ethylpiperazin-1-yl)-2-nitroaniline

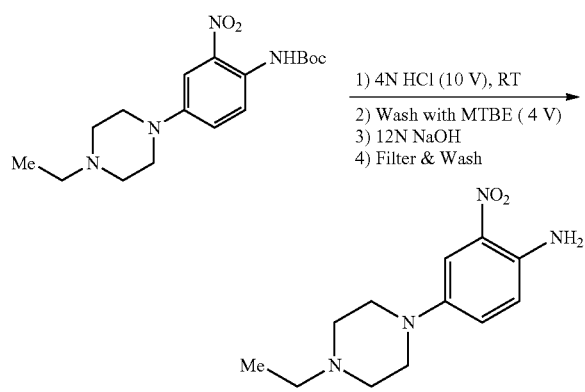

To a suspension of tert-butyl 4-(4-ethylpiperazin-1-yl)-2-nitrophenylcarbamate (210 g, 599 mmol) in a minimal amount of toluene was charged 4N aqueous HCl (2.1 L, 14 equiv) with mechanical stirring, maintaining the internal temperature at ≤40° C. The resulting slurry was stirred at room temperature with a nitrogen sweep to remove any remaining organic solvent until HPLC analysis indicated complete reaction. To the suspension was added MTBE (1 L). The mixture was agitated for 30 mins and the layers were separated. The lower aqueous layer was cooled to 0-5° C. and 12N aqueous NaOH solution was added to pH 9-10 (ca. 480 mL required). The resulting solid was filtered and washed with cold (0-5° C.) water (3×400 mL). The wet cake was filtered under vacuum and/or nitrogen sweep at 30° C. to afford the title compound (136.3 g, 91% yield) as a red solid.

tert-Butyl 4-bromo-2-nitrophenylcarbamate—Alternate Procedure

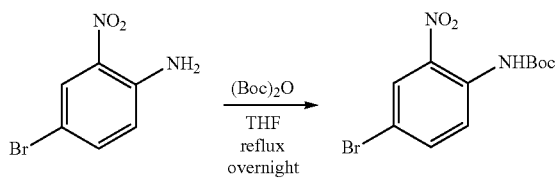 [SMILES: "(Boc)2O" ; Nc1ccc(Br)cc1[N+](=O)[O-] ; CC(C)(C)OC(=O)Nc1ccc(Br)cc1[N+](=O)[O-]]

A mixture of 4-bromo-2-nitroaniline (4 g, 18.4 mmol) and (Boc)₂O (4.4 g, 20.24 mmol) in THF (50 mL) was heated under reflux overnight. The mixture was concentrated and the residue was purified by flash chromatography on silica eluting with PE:EtOAc=20:1 to obtain the title compound (5.4 g, yield: 93%). MS (ESI): 317, 319 [M+H]⁺.

tert-Butyl 4-(4-ethylpiperazin-1-yl)-2-nitrophenyl-carbamate—Alternate Procedure A degassed mixture of tert-butyl 4-bromo-2-nitrophenyl-carbamate (5.4 g, 17 mmol), 1-ethylpiperazine (2.91 g, 25.5 mmol), Pd₂(dba)₃ (2.1 g, 3.4 mmol), xantphos (3.92 g, 6.8 mmol) and Cs₂CO₃ (11.1 g, 34 mmol) in toluene (85 mL) was heated at 100° C. for 4 hours. The reaction was concentrated, and the residue was purified by flash chromatography on silica eluting with MeOH:DCM=1:50-1:20 to obtain the title compound (3.3 g, yield: 55%). MS (ESI): 351 [M+H]⁺.

a. 1-(6-chloropyrimidin-4-yl)-3-(2,6-dichloro-3,5-dimethoxyphenyl)-1-methylurea

A 3 L 3-necked round bottom flask was charged with 2,6-dichloro-3,5-dimethoxyaniline (199.65 g, 899 mmol), triphosgene (93 g, 315 mmol, 0.35 equiv), and 1,4-dioxane (1.9 L). The mixture was heated to 100° C. and stirred at this temperature for 3.5 h. The mixture was then cooled to 20-25° C., and filtered. The solid residue was washed with 1,4-dioxane (200 mL). The filtrate was concentrated to a minimal stirrable volume and chased 3× with dioxane (700 mL each chase). The solution was concentrated to a minimal stirrable volume following the last chase and then redissolved in 1,4-dioxane (730 mL). To this slurry was charged 6-chloro-N-methylpyrimidin-4-amine (129 g, 899 mmol, 1 equiv). The resulting mixture was heated to 80° C. and stirred at this temperature for 60 h, during which time a substantial amount of precipitate formed. The mixture was cooled to 20-22° C. and filtered. The solid cake was washed with dioxane (2×90 mL) and dried under vacuum at room temperature with a nitrogen sweep to afford the title compound (191 g, 54% yield) as a solid.

b. 1-(6-chloropyrimidin-4-yl)-3-(2,6-dichloro-3,5-dimethoxyphenyl)-1-methyl-3-((2-(trimethylsilyl)ethoxy)methyl)urea

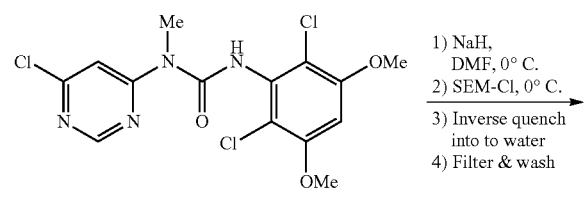

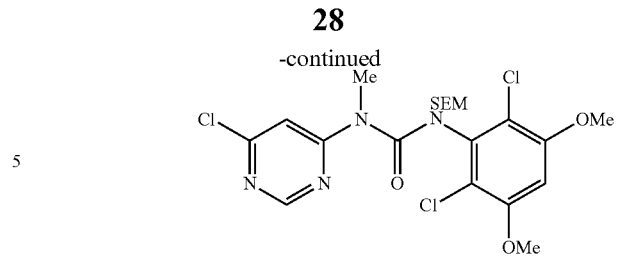

A 5 L 3-necked round bottom flask was charged with 3-(2,6-Dichloro-3,5-dimethoxyphenyl)-1-(6-(4-(4-ethylpiperazin-1-yl)-2-nitrophenylamino)pyrimidin-4-yl)-1-methylurea (135 g, 345 mmol), potassium iodide (6.87 g, 41.4 mmol. 0.12 equiv) and DMF (400 mL). The mixture was cooled to 0-5° C. and NaH (60% dispersion in mineral oil, 17.9 g, 448 mmol, 1.3 equiv) was charged portionwise so as to maintain the internal temperature at ≤5° C. The mixture was allowed to stir for 1 hour at 0-5° C., after which SEM-Cl (73.2 mL, 414 mmol, 1.2 equiv) was added dropwise so as to maintain the internal temperature at ≤5° C. The reaction mixture was stirred at 0-5° C. until HPLC analysis indicated complete reaction (ca. 1 h). The batch was transferred to a second 5 L 3-necked round bottom flask containing cold (0-5° C.) water (4 L). The resulting slurry was stirred for 15 mins, then filtered. The cake was washed with water (3×300 mL) and dried under vacuum to afford the title compound (184 g, 102%) as a solid.

c. 1-(2,6-dichloro-3,5-dimethoxyphenyl)-3-(6-((4-(4-ethylpiperazin-1-yl)-2-nitro phenyl) amino)pyrimidin-4-yl)-3-methyl-1-((2-(trimethylsilyl)ethoxy)methyl)urea

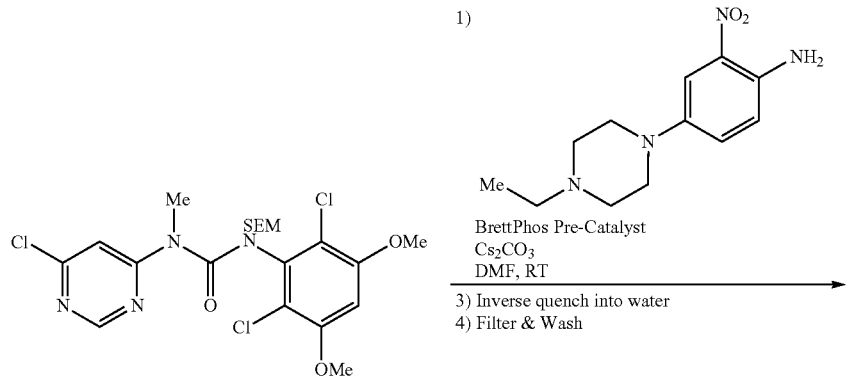

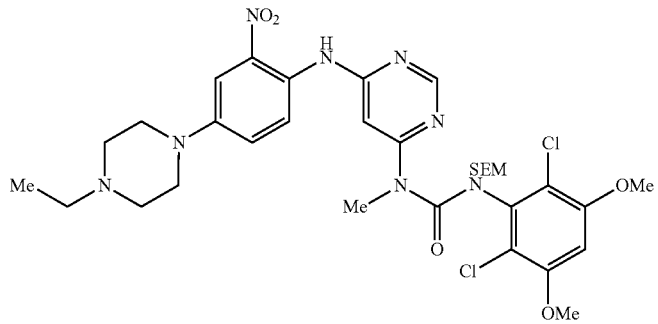

A 3 L 3-necked round bottom flask was charged with 1-(6-chloropyrimidin-4-yl)-3-(2,6-dichloro-3,5-dimethoxyphenyl)-1-methyl-3-((2-(trimethylsilyl)ethoxy)methyl)urea (182 g, 349 mmol), 4-(4-ethylpiperazin-1-yl)-2-nitroaniline (87 g, 349 mmol, 1 equiv), BrettPhos Pre-catalyst (CAS #1470372-59-8, 15.6 g, 17.2 mmol, 0.05 equiv), and cesium carbonate (136 g, 418 mmol, 1.2 equiv). The system was flushed with nitrogen and previously degassed DMF (910 mL) was added. The solution was sparged with nitrogen gas for 30 mins, then allowed to stir at 22-25° C. until HPLC analysis indicates complete reaction (3-4 hours). The mixture was charged into a 5 L 3-necked round bottom flask containing water (2.7 L) at such a rate as to maintain the internal temperature at ≤35° C. The resulting slurry was cooled to 22-25° C. then filtered. The cake was washed with water (4×150 mL) and dried under vacuum to afford the title compound (257 g, 100% yield) as a solid.

d. Synthesis of 1-(2,6-dichloro-3,5-dimethoxyphenyl)-3-(6-((4-(4-ethylpiperazin-1-yl)-2-nitro phenyl)amino)pyrimidin-4-yl)-3-methyl-1-((2-(trimethylsilyl)ethoxy)methyl)urea—Alternate Procedure

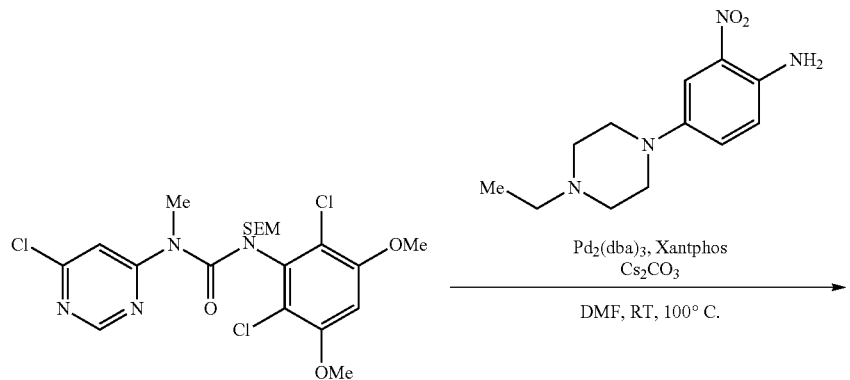

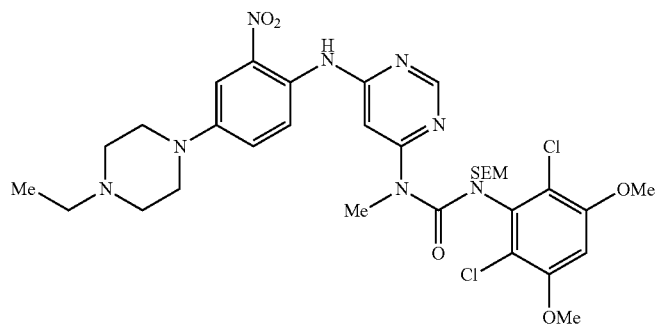

To a 3 L four necked round bottom flask equipped with reflux condenser, magnetic stirrer and nitrogen purging set up, was added 4-(4-ethylpiperazin-1-yl)-2-nitroaniline (50 g, 0.199 mol), 1-(6-chloropyrimidin-4-yl)-3-(2,6-dichloro-3,5-dimethoxyphenyl)-1-methyl-3-((2-(trimethylsilyl)ethoxy)methyl)urea (125.1 g, 0.239 mol, 1.2 equiv), DMF (500 mL) and cesium carbonate (130.17 g, 0.399 mol, 2.0 equiv). The resulting mixture was purged by bubbling nitrogen through the mixture for 5-10 min at room temperature. To the mixture were added $Pd_2(dba)_3$ (18.29 g, 0.0199 mol, 0.10 equiv), Xantphos (11.55 g, 0.0199 mol, 0.10 equiv), and nitrogen purging was continued for another 10 min. The reaction mixture was then heated to 100° C. until TLC analysis indicated complete reaction (ca. 2 h). The mixture was filtered through a celite bed and an aqueous workup was performed, the desired product being extracted with EtOAc (3×500 mL). The combined organic phases were washed with brine solution (2×500 mL), dried over $Na_2SO_4$, and concentrated to provide the title compound as a reddish solid (142 g) which was carried forward as is.

e. 1-(6-(2-Amino-4-(4-ethylpiperazin-1-yl)phe-nylamino)pyrimidin-4-yl)-3-(2,6-dichloro-3,5-dime-thoxyphenyl)-1-methylurea

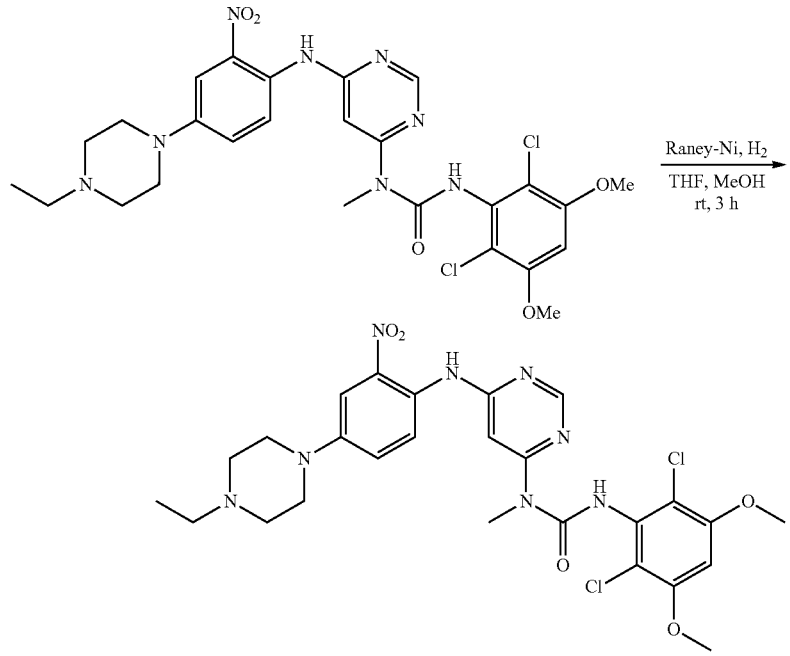

To a solution of 3-(2,6-dichloro-3,5-dimethoxyphenyl)-1-(6-(4-(4-ethylpiperazin-1-yl)-2-nitrophenylamino)pyrimidin-4-yl)-1-methylurea (330 mg, 0.546 mmol) in THF (20 mL) and MeOH (20 mL) was added Raney-Ni (suspension in water) at room temperature, the resulting mixture was stirred for 3 hours under hydrogen atmosphere (1 atm). The reaction was filtered and concentrated. The residue was washed twice with MeOH to obtain the title compound (280 mg, purity: 90%), which was used directly in the next step. MS (ESI): 575 [M+H]$^+$.

f. Preparation of N-(2-(6-(3-(2,6-Dichloro-3,5-dime-thoxyphenyl)-1-methylureido)pyrimidin-4-ylamino)-5-(4-ethylpiperazin-1-yl)phenyl)acrylamide

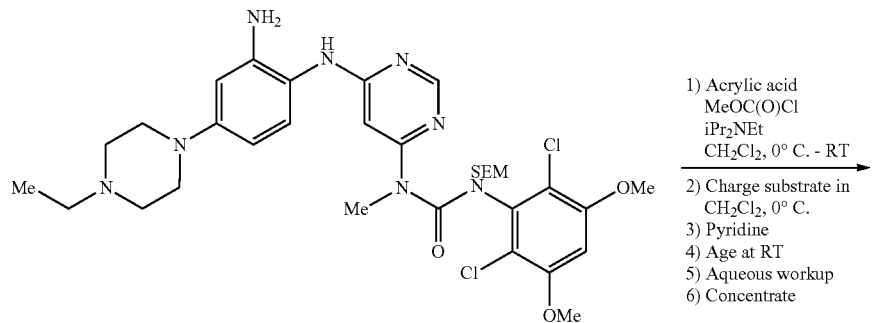

-continued

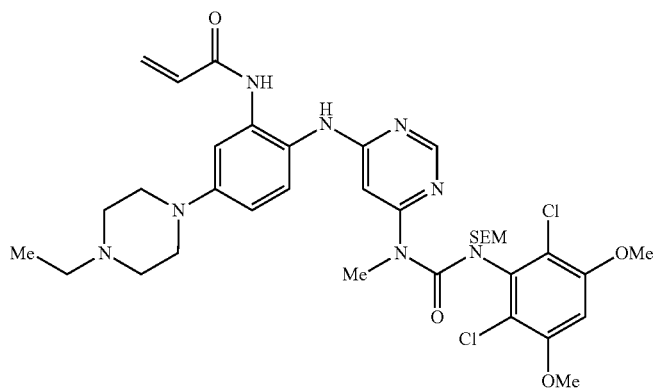

A 5 L 3-necked round bottom flask was charged with dichloromethane (1 L), acrylic acid (14.6 mL, 213 mmol, 1.5 equiv), and Hunig's base (39.5 mL, 227 mmol, 1.6 equiv). The solution was cooled to 0-5° C. and treated with methyl chloroformate (15.4 mL, 198 mmol, 1.4 equiv) at such a rate as to maintain the internal temperature at ≤7° C. The mixture was warmed to 20-25° C. and stirred at this temperature for 1 h, then cooled to 0-5° C. In a separate 500 mL round bottom flask was dissolved 1-(6-((2-amino-4-(4-ethylpiperazin-1-yl)phenyl)amino)pyrimidin-4-yl)-3-(2,6-dichloro-3,5-dimethoxyphenyl)-1-methyl-3-((2-(trimethylsilyl)ethoxy)methyl)urea (100 g, 142 mmol, 1 equiv) in dichloromethane (150 mL). The substrate solution was transferred the to the mixed anhydride solution, rinsing with dichloromethane (200 mL) and transferring this rinse to the anhydride solution as well. To the resulting mixture was added pyridine (27.5 mL, 340 mmol, 2.4 equiv) and the resulting mixture was warmed to 20-25° C. The reaction mixture was stirred at this temperature until HPLC analysis indicated complete reaction (ca. 1 h). The mixture was then cooled to 0-5° C. and saturated aqueous $NaHCO_3$ solution (1 L) was added. The batch was agitated for 20 mins, then the phases were settled and split. settle. The lower organic phase was washed a second time with $NaHCO_3$ solution (600 mL). The lower organic phase was then washed with 10% aqueous NaCl solution (600 mL). The lower organic phase was dried over solid $Na_2SO_4$ (250 g), filtered, and concentrated to afford the title compound (108 g, 100%) which was used in the next step without purification.

g. Synthesis and Crystallization of Free Base Form of Compound 108

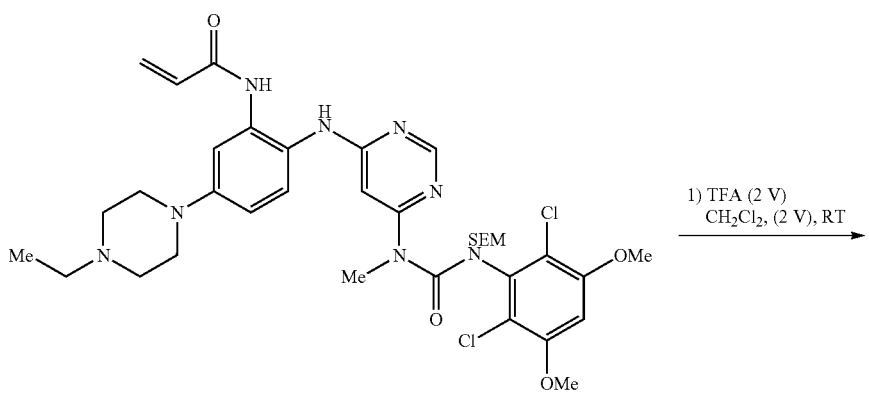

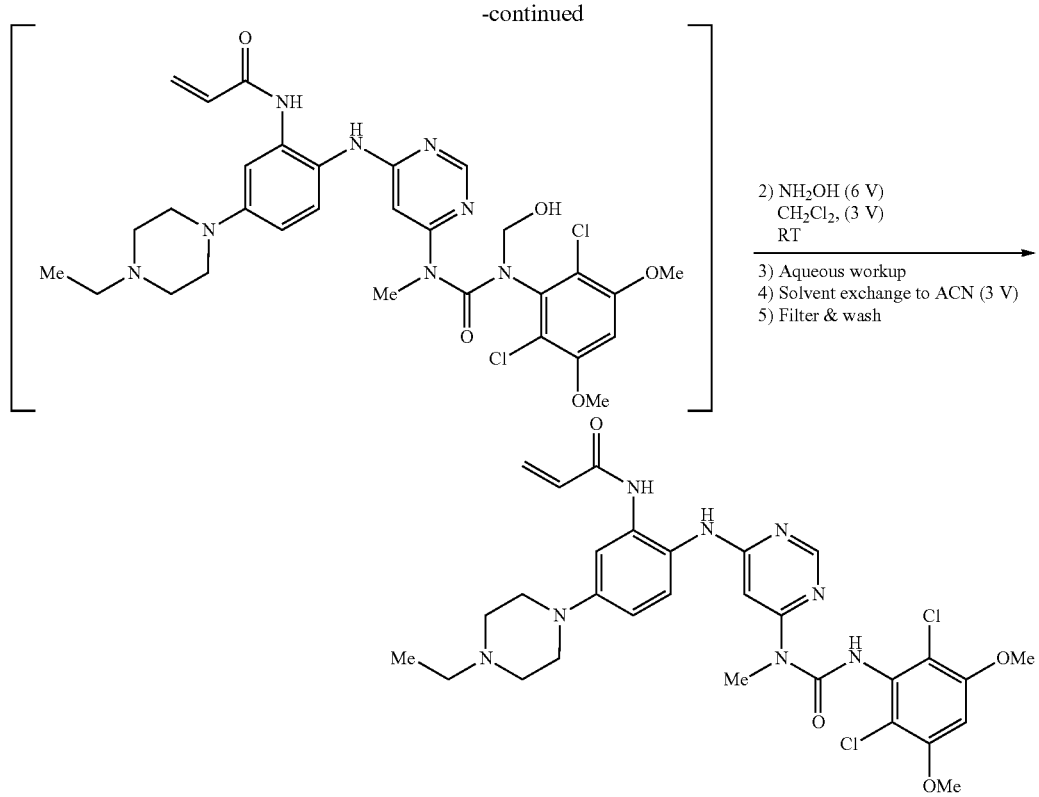

Crystalline Free Base Form of Compound 108

Figure 9A:
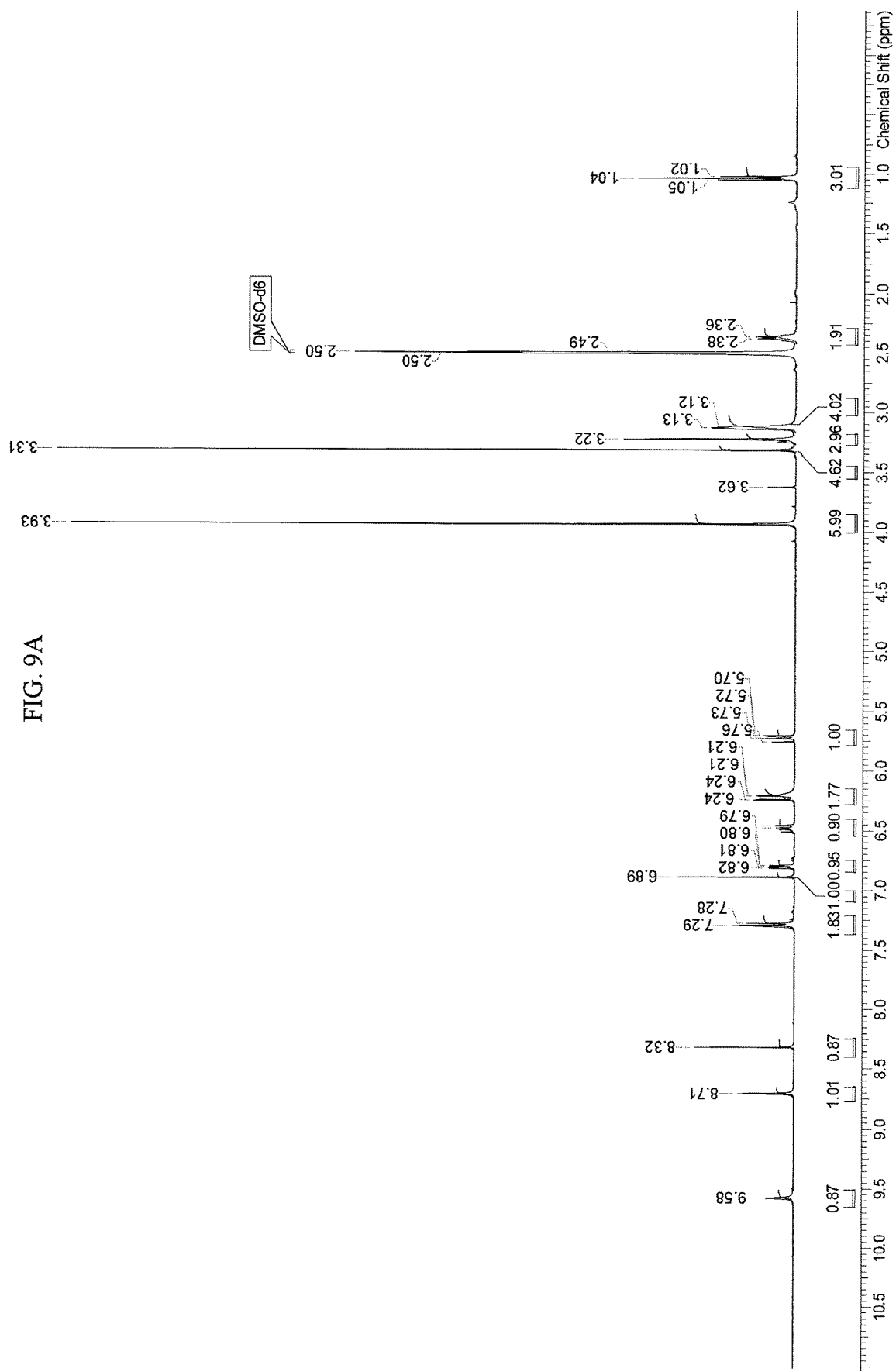
FIGS. 9A-9D present $^1$H-NMR spectrum consistent with the structure of Compound 108.
Figure 9B:
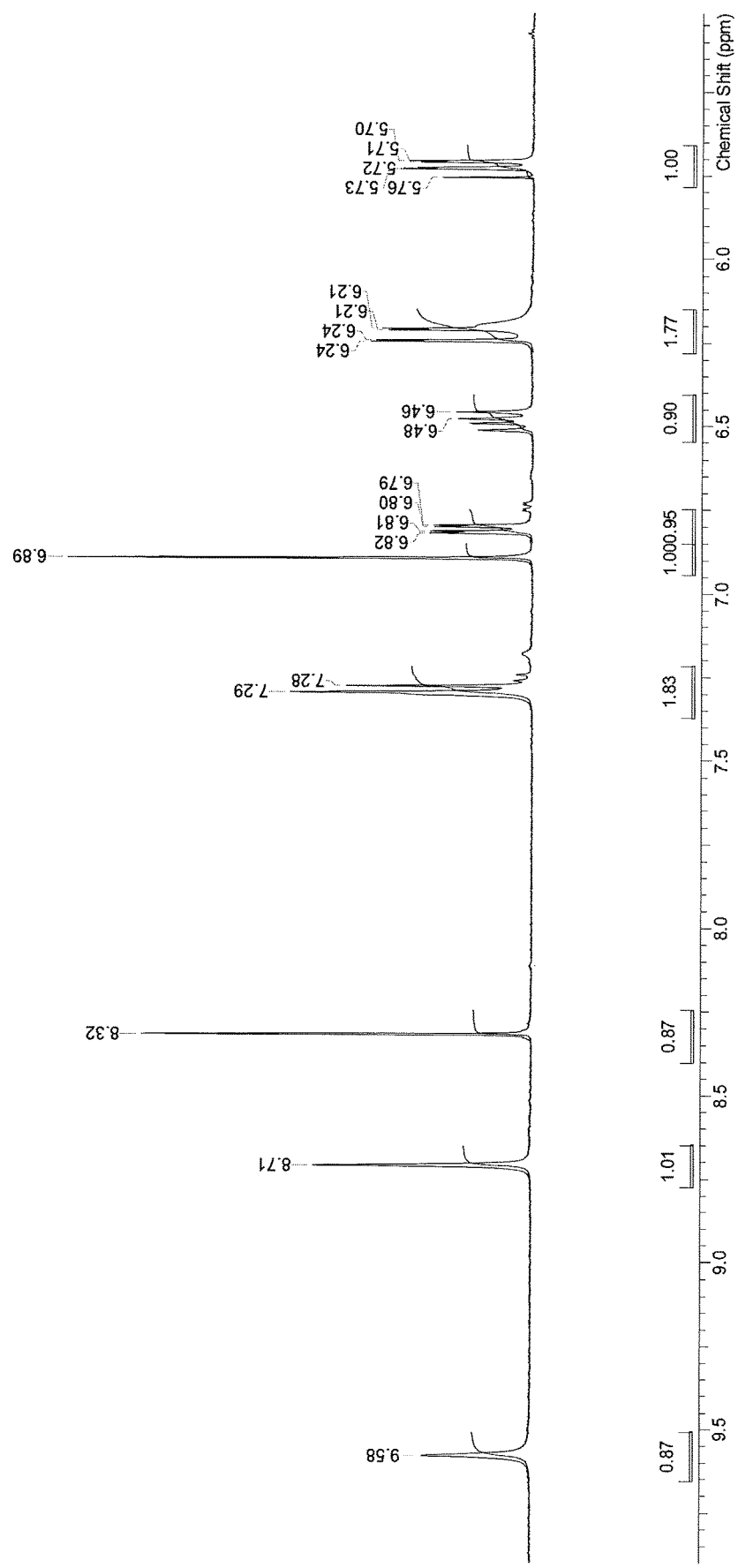
Figure 9C:
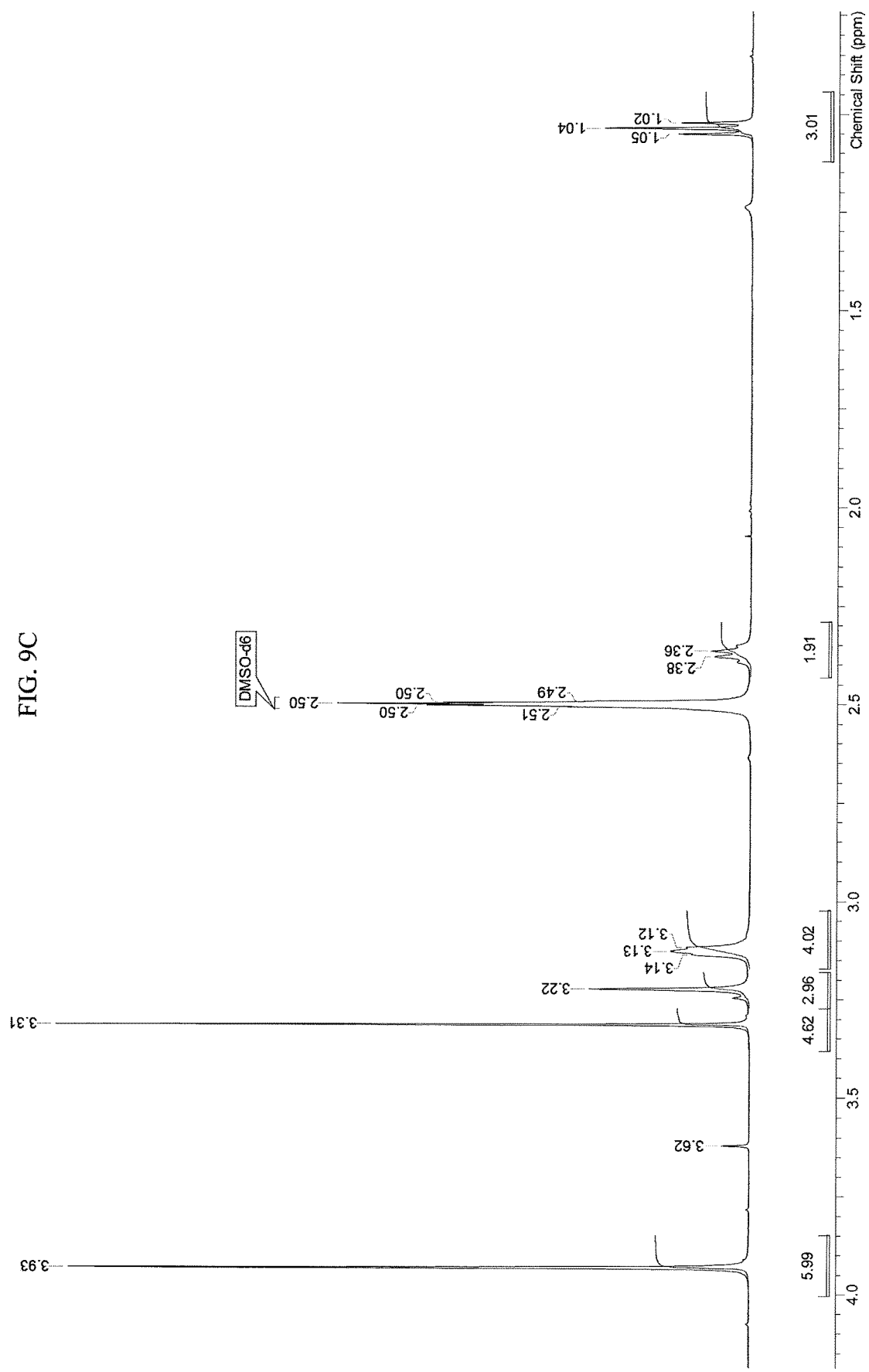

A stirred solution of N-(2-((6-(3-(2,6-dichloro-3,5-dimethoxyphenyl)-1-methyl-3-((2-(trimethylsilyl)ethoxy)methyl)ureido)pyrimidin-4-yl)amino)-5-(4-ethylpiperazin-1-yl)phenyl)acrylamide (1, 51 g, 67.12 mol) in dichloromethane (102 mL) was cooled to 0-5° C. To this solution was added trifluoroacetic acid (102 mL, 1585 mol, 23.6 equiv) at such rate as to maintain the internal temperature ≤15° C. Once addition was complete, the mixture was allowed to warm to room temperature and stirred for 3h, at which point HPLC analysis indicated complete reaction. The mixture was transferred to a second flask containing cold (0-5° C.) saturated ammonium hydroxide solution (550 mL), at such a rate as to maintain internal temperature ≤25° C. The mixture was allowed to stir for 5-10 mins, at which HPLC analysis indicated complete reaction. The mixture was transferred to a separatory funnel and extracted twice with dichloromethane/methanol (5:1, 600 mL) and once with dichloromethane/methanol (5:1, 300 mL). The combined organic phases were concentrated to a minimum stirrable volume and acetonitrile (150 mL) was added. The resulting solid was slurried for 15 mins, then filtered. The solid cake was washed with acetonitrile (4×30 mL) and dried on the filter under vacuum with a nitrogen sweep to afford N-(2-((6-(3-(2,6-dichloro-3,5-dimethoxyphenyl)-1-methylureido)pyrimidin-4-yl)amino)-5-(4-ethylpiperazin-1-yl)phenyl)acrylamide (108, 29.56 g, 70% yield) as a solid. $^1$H-NMR (d$_6$-DMSO): δ 1.04 (t, J=7.15 Hz, 3H); 2.37 (m, 2H); 3.13 (m, 4H); 3.22 (m, 4H); 3.31 (s, 3H); 3.93 (s, 6H); 5.72 (dd, 1H, J=10.27, 1.83 Hz); 6.23 (dd, 1H, J=17.06, 1.83 Hz; br s, 1H); 6.48 (dd, 1H, J=16.87, 10.27 Hz); 6.81 (dd, 1H, J=8.99, 2.75 Hz); 6.89 (s, 1H); 7.29 (br d, J=9.17 Hz, 2H); 8.32 (s, 1H); 8.71 (s, 1H); 9.58 (s, 1H) (FIGS. 9A-9C). Mass spec: [M+H]$^+$=629.2. This was determined on a Varian Inova at 500 MHz.

Recrystallization of Free Base Form of Compound 108:

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide (108, 42 g) was dissolved in dichloromethane/methanol (4:1, 500 mL). To this solution was added acetonitrile (150 mL). The mixture was concentrated under reduced pressure to a total volume of 150 mL. To the resulting mixture was added additional acetonitrile (150 mL) and the mixture was again concentrated under reduced pressure to a total volume of 150 mL. The resulting slurry was filtered. The solid cake was washed with acetonitrile (4×30 mL) and dried on the filter under vacuum with a nitrogen sweep to afford recrystallized free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide (108, 36 g, 86% recovery from recrystallization) as a solid.

Example 4: Characterization of Crystalline Free Base Form of Compound 108 by Powder X-Ray Diffraction (PXRD)

PXRD data for samples in this Example were taken on a Rigaku MultiFlex Instrument (Target: Cu; Tube voltage: 40 kV; Tube current: 30 mA, Range 3.0-45.0=42.0°). Samples were prepared by adding powders into standard round aluminum specimen holders and leveled with a glass slide.

A crystalline free base form of Compound 108 is characterized by the PXRD pattern shown in FIG. 5, truncated to show a range of 3.0-35.0=32.0°. An overlay of the PXRD spectra from three lots of crystalline free base form of Compound 108 (FIG. 6) demonstrates the reproducibility.

As summarized in Table 7, the crystalline free base form of Compound 108 exhibits a PXRD pattern with six characteristic peaks.

TABLE 7

Characteristic crystalline free base form Compound 108 PXRD Peaks
2θ° (±0.2°)

| |
|---|
| 8.0 |
| 9.5 |
| 10.3 |
| 14.8 |
| 16.5 |
| 17.1 |
| 19.3 |
| 21.8 |
| 23.7 |
| 24.5 |

Example 5: Characterization of Crystalline Free Base Form Compound 108 by Differential Scanning Calorimetry (DSC)

DSC for samples in this example was taken on a Mettler-Toledo DSC 1/700 (Run conditions: Initial temperature 35° C., Final temp 325° C., Heating rate 10° C./min).

Approximately 4 to 8 mg of crystalline free base form of Compound 108 was added to a 70 µL Aluminum pan, covered, crimped and pierced with a single hole. The sample and a blank vessel prepared in the same manner were added to the thermocouple surface and the instrument was equilibrated at the initial temperature. The chamber was heated to 325° C. at 10° C./min and the differential thermogram was collected.

Figure 8:
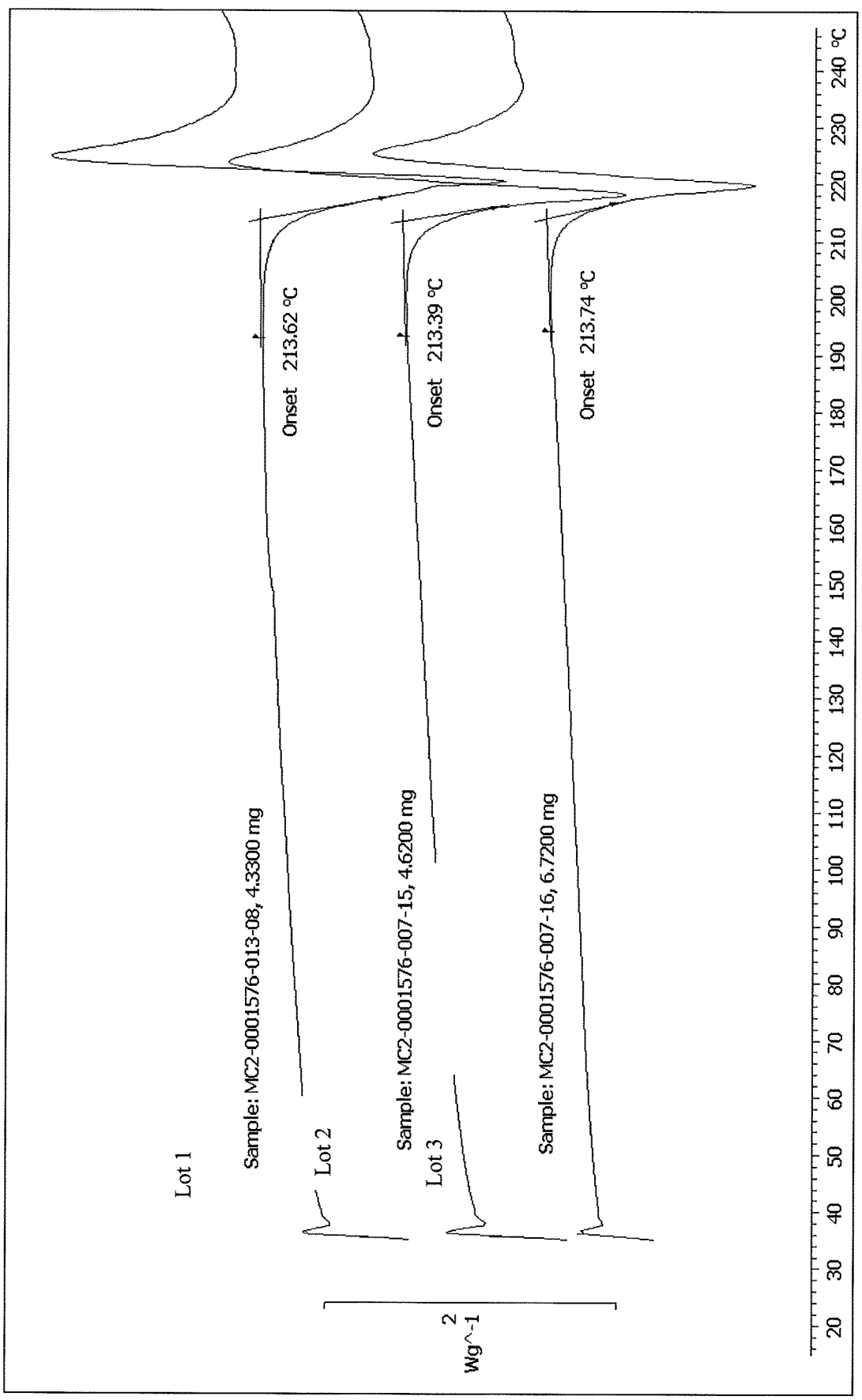
FIG. 8 presents an overlay of DSC curves for three lots of crystalline free base form of Compound 108.

A differential thermogram of crystalline free base form of Compound 108 was obtained using a Differential Scanning Calorimetry (DSC) Instrument (see FIG. 7, truncated after about 254° C.). The crystalline free base form of Compound 108 is characterized by having a single endothermic peak at an onset temperature of 213.6° C. (±1° C.). A comparison of onset temperatures from three different batches of the crystalline free base form of Compound 108 is shown in Table 8 and FIG. 8 (truncated after about 246° C.).

TABLE 8

Comparison of Onset Temperatures From Three Lots

| Crystalline Free Base Form of Compound 108 Lot | Onset (° C.) |
|---|---|
| 1 | 213.62 |
| 2 | 213.39 |
| 3 | 213.74 |
| Mean | 213.6 |
| Range | 0.35 |

Example 6: Solubility of Crystalline Free Base Form Compound 108

The solubility of crystalline free base form compound 108 in 0.1 N HCl was 5.2 mg/mL.

Example 7

This example reports additional data prepared from a separate batch of crystalline free base form of Compound 108, than the material giving rise to the data reported above.

Figure 10:
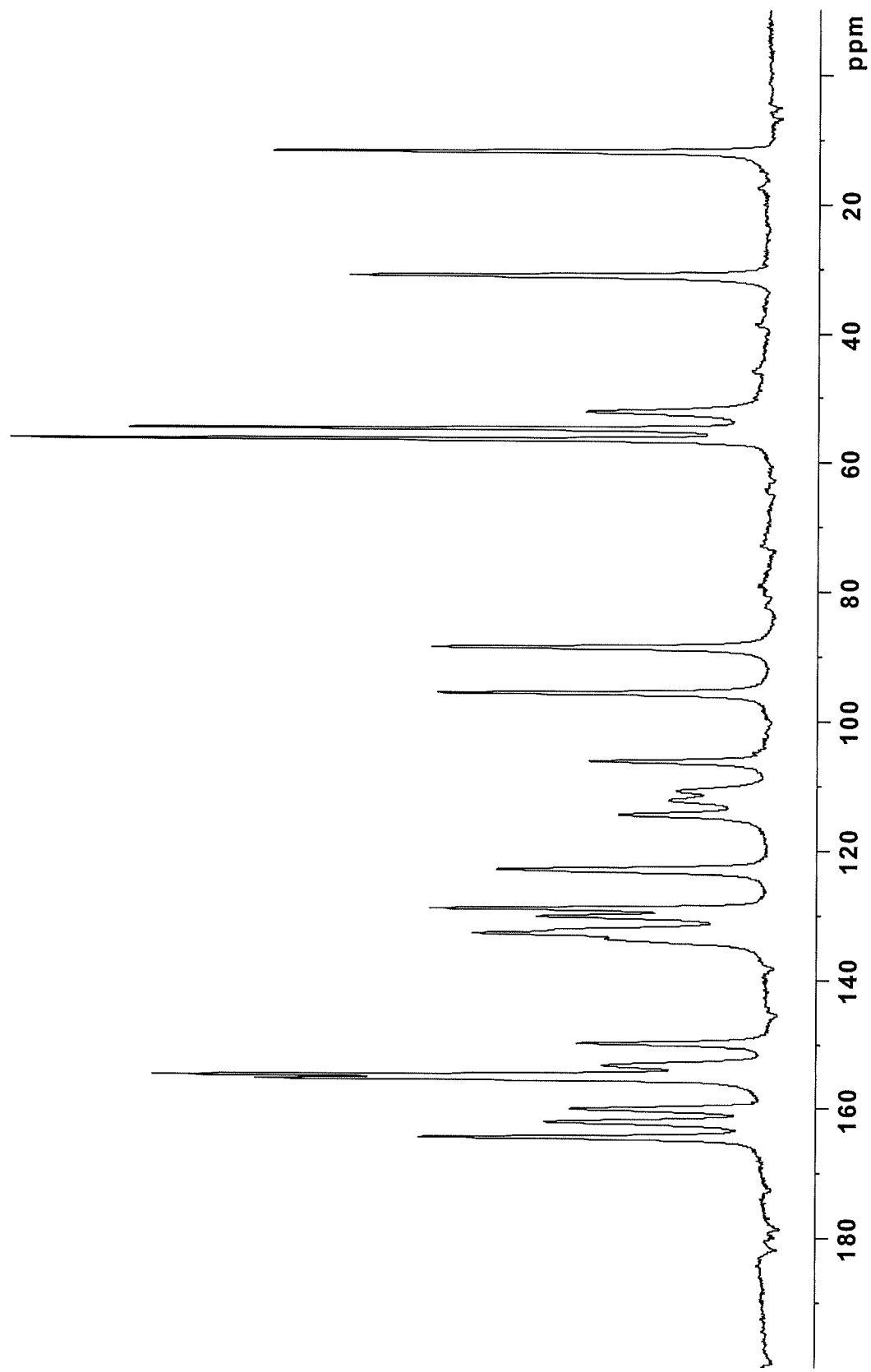
FIG. 10 presents a $^{13}$C-NMR spectrum of crystalline free base form of Compound 108.

$^{13}$C-NMR (100 MHz, solid state) δ(ppm): 11.9, 31.1, 52.2, 54.8, 56.5, 88.6, 95.7, 106.2, 110.8, 112.3, 114.5, 123.0, 129.0, 130.3, 132.3, 132.9, 133.8, 149.9, 153.2, 154.8, 155.4, 160.0, 162.1, 164.4. This is shown in FIG. 10.

Figure 9D:
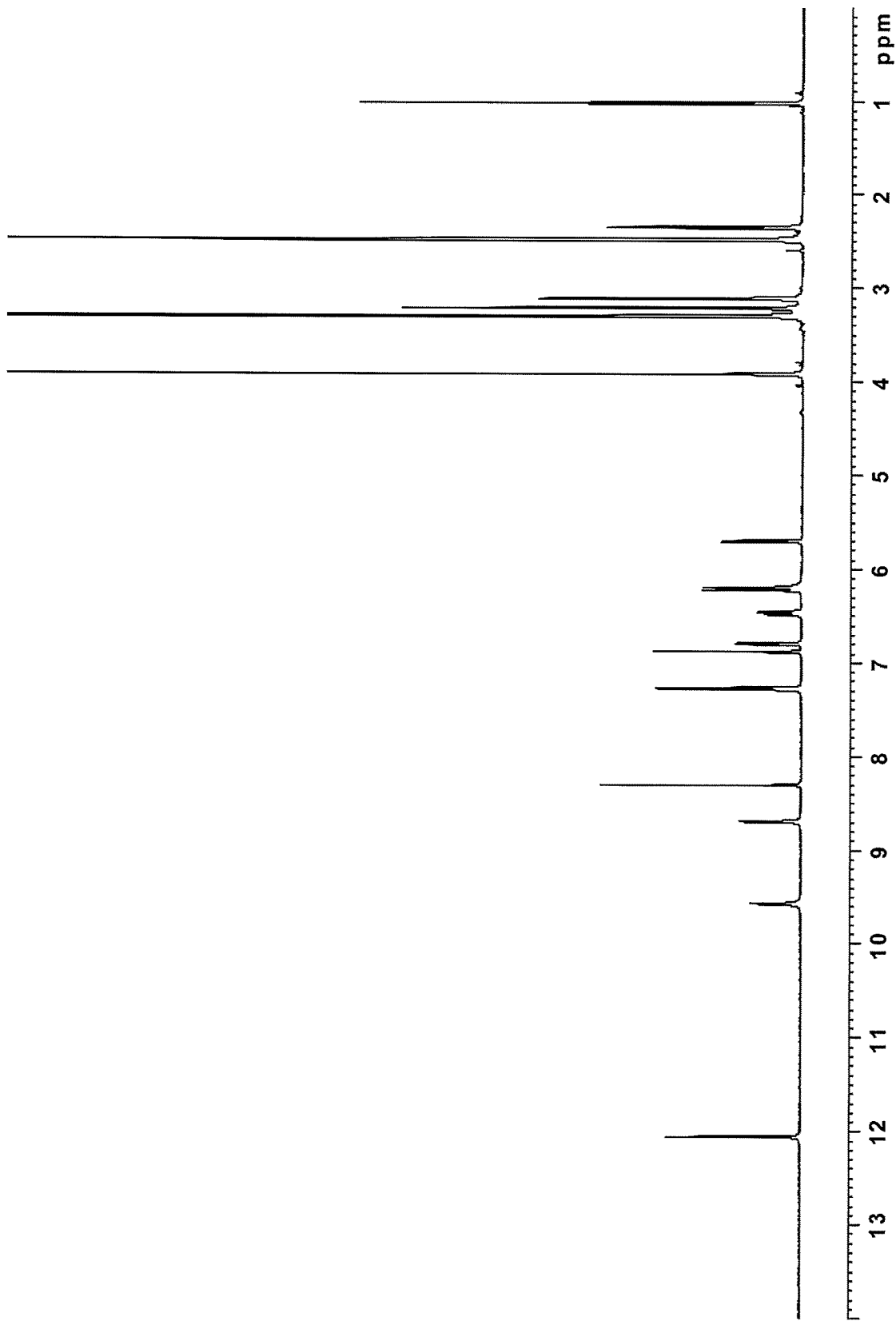

$^1$H-NMR spectrum (DMSO-$d_6$) δ(ppm): 1.03 (3H, t, J=7.2 Hz), 2.37 (2H, q, J=7.2 Hz), 2.46-2.51 (4H, m), 3.12 (4H, t, J=5.0 Hz), 3.21 (3H, s), 3.92 (6H, s), 5.71 (1H, dd, J=10.3, 1.7 Hz), 6.13-6.26 (1H, m), 6.22 (1H, dd, J=17.1, 1.8 Hz), 6.48 (1H, dd, J=17.0, 10.3 Hz), 6.80 (1H, dd, J=8.9, 2.6 Hz), 6.88 (1H, s), 7.23-7.33 (1H, m), 7.28 (1H, d, J=8.9 Hz), 8.30 (1H, s), 8.69 (1H, brs), 9.57 (1H, brs), 12.05 (1H, s). This was measured using an Avance 600 MHz (Bruker). This is shown in FIG. 9D.

Example 8: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride Crystals A solution (4 mL) of acetone containing 10% (v/v) DMSO was spiked with hydrochloric acid solution (2.76 µL, 1 eq), added to N-(2((6-(3-(2,6-dichloro-3,5-dimethoxyphenyl)-1-methylureido)pyrimidin-4-yl)amino)-5-(4-ethylpiperazin-1-yl)phenyl)acrylamide (20.25 mg), irradiated with ultrasound, and stirred at room temperature for 7 days. Resultant crystals were filtered off and washed with acetone to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride crystals.

Example 9: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride Crystals A solution (2.5 mL) of acetone containing 10% (v/v) DMSO was spiked with hydrochloric acid solution (7.25 µL, 1 eq), added to N-(2((6-(3-(2,6-dichloro-3,5-dimethoxyphenyl)-1-methylureido)pyrimidin-4-yl)amino)-5-(4-ethylpiperazin-1-yl)phenyl)acrylamide (53.12 mg), irradiated with ultrasound, and stirred at room temperature for a day. Crystalline form obtained in Example 8 was added to the reaction mixture and further stirred for 5 days. Resultant crystals were filtered off and washed with ethanol (1 mL) to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride crystals (50.60 mg).

Example 10: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride Crystals A solution (25 mL) of acetone containing 10% (v/v) DMSO was spiked with hydrochloric acid solution (68.51 µL, 1 eq), added to N-(2((6-(3-(2,6-dichloro-3,5-dimethoxyphenyl)-1-methylureido)pyrimidin-4-yl)amino)-5-(4-ethylpiperazin-1-yl)phenyl)acrylamide (502.1 mg), and irradiated with ultrasound. Crystalline form obtained in Example 9 was added to the reaction mixture and stirred at room temperature for 7 days. Resultant crystals were filtered off, washed with ethyl acetate (1.5 mL) and dried under reduced pressure for 3 days to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride crystals (543.0 mg).

Figure 11:
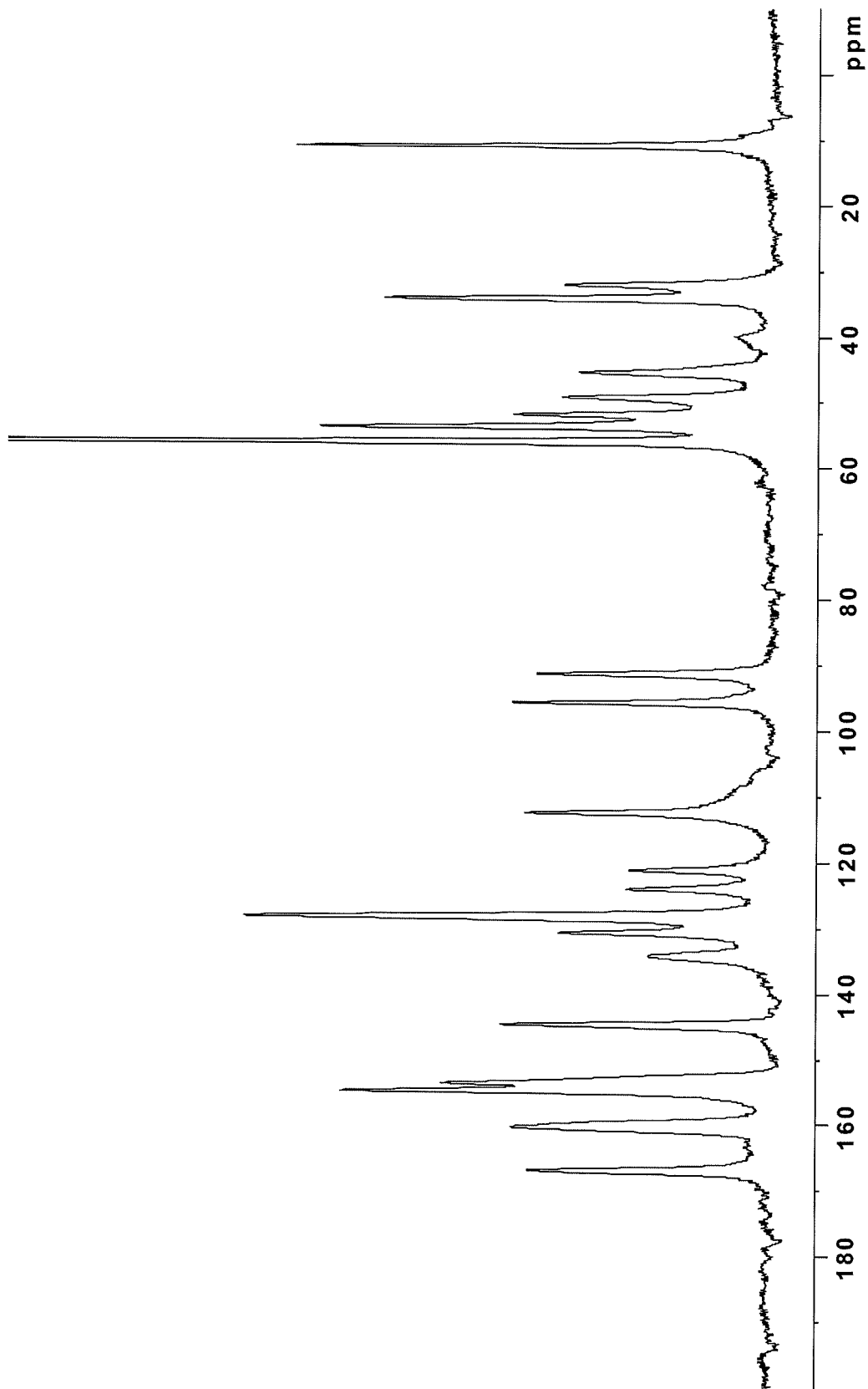
FIG. 11 presents $^{13}$C-NMR spectrum of crystalline N-(2-((6-(3-(2,6-dichloro-3,5-dimethoxyphenyl)-1-methylureido)pyrimidin-4-yl)amino)-5-(4-ethylpiperazin-1-yl)phenyl) acrylamide monohydrochloride (i.e. the crystalline monohydrochloride salt form of Compound 108) obtained in Example 10 herein.

¹³C-NMR (100 MHz, solid state) δ(ppm): 10.9, 32.1, 34.1, 45.4, 49.2, 51.9, 53.7, 56.0, 91.3, 95.7, 112.5, 121.2, 124.1, 128.2, 130.7, 134.3, 144.7, 153.6, 154.8, 160.3, 166.9. This is shown in FIG. 11.

Figure 12:
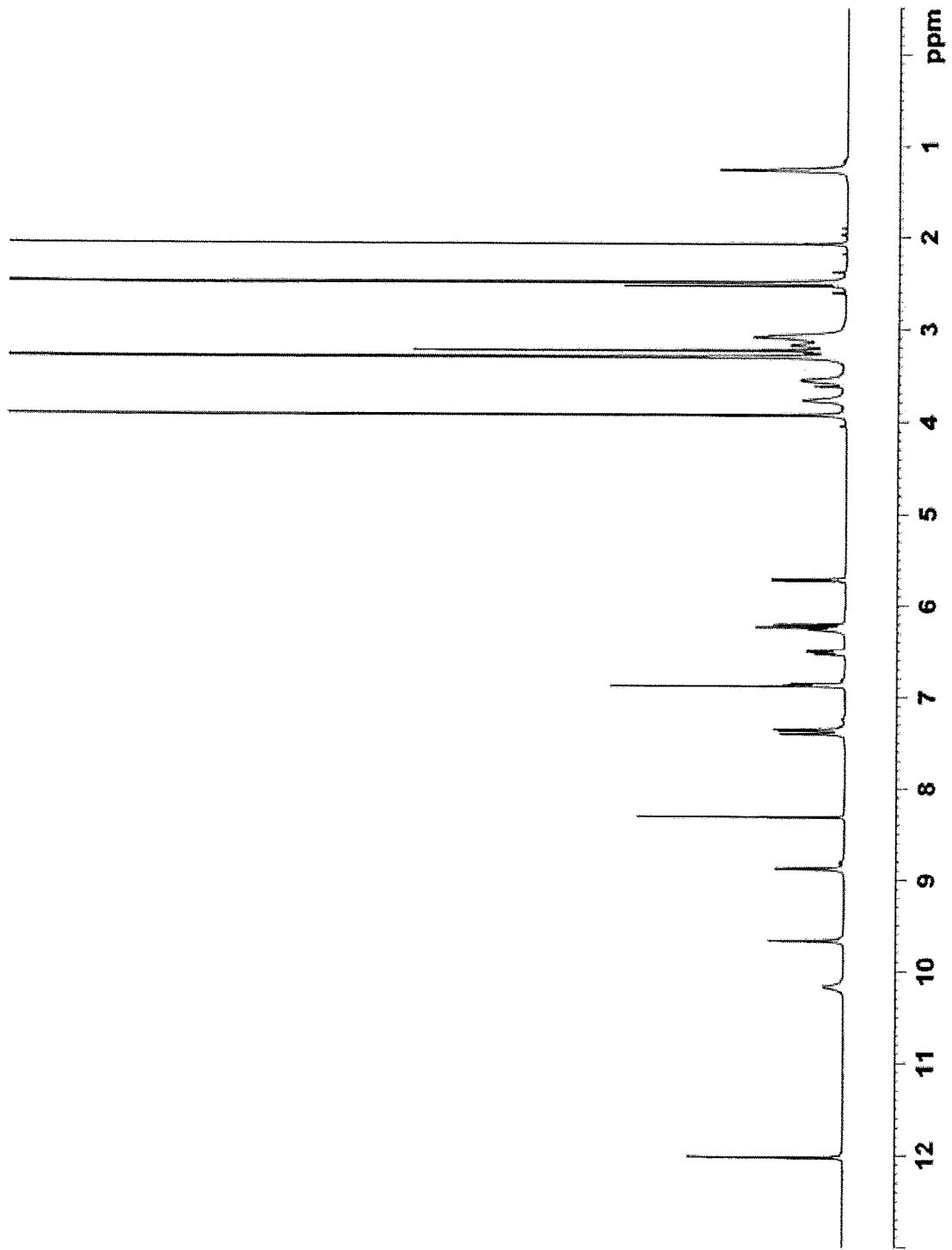
FIG. 12 presents a $^1$H-NMR spectrum of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride obtained in Example 10 herein.

¹H-NMR spectrum (DMSO-$d_6$) δ(ppm): 1.26 (3H, m), 2.98-3.21 (6H, m), 3.23 (3H, s), 3.55 (2H, brs), 3.77 (2H, brs), 3.92 (6H, s), 5.72 (1H, dd, J=10.3, 1.3 Hz), 6.23 (1H, dd, J=17.0, 1.6 Hz), 6.26 (1H, brs), 6.52 (1H, dd, J=17.0, 10.2), 6.87 (1H, dd, J=9.0, 2.0 Hz), 6.89 (1H, s), 7.37 (1H, d, J=8.8 Hz), 7.41 (1H, brs), 8.32 (1H, s), 8.88 (1H, s), 9.67 (1H, s), 10.17 (1H, brs), 12.02 (1H, s). This is shown in FIG. 12.

Example 11

PXRD data for samples in this Example were taken on a Rigaku RINT TTR-III Instrument (Target: Cu; Tube voltage: 50 kV; Tube current: 300 mA, Range 5.0-35.0=30°).

A crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide monohydrochloride as prepared in Example 10 is characterized by the PXRD pattern shown in FIG. 13.

As summarized in Table 8, the crystalline form of N-(2-((6-(3-(2,6-dichloro-3,5-dimethoxyphenyl)-1-methylureido)pyrimidin-4-yl)amino)-5-(4-ethylpiperazin-1-yl)phenyl) acrylamide monohydrochloride exhibits a PXRD pattern with at least ten characteristic peaks.

TABLE 8

Characteristic crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide 2θ° (±0.2°)

| |
|---|
| 9.0 |
| 11.3 |
| 18.1 |
| 19.9 |
| 23.0 |
| 23.5 |
| 25.4 |
| 26.6 |
| 27.6 |
| 29.0 | monohydrochloride PXRD Peaks.

Example 12: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride Crystals Acetone (3 mL) was spiked with hydrochloric acid solution (12.36 μL, 3 eq), added to N-(2((6-(3-(2,6-dichloro-3,5-dimethoxyphenyl)-1-methylureido)pyrimidin-4-yl) amino)-5-(4-ethylpiperazin-1-yl)phenyl)acrylamide (30.19 mg), irradiated with ultrasound, and stirred at room temperature for 4 days. Resultant crystals were filtered off to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride crystals.

Example 13: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride Crystals A solution (10 mL) of acetone containing 10% (v/v) DMSO was spiked with hydrochloric acid solution (137.7 μL, 2 eq), added to N-(2((6-(3-(2,6-dichloro-3,5-dimethoxyphenyl)-1-methylureido)pyrimidin-4-yl)amino)-5-(4-ethylpiperazin-1-yl)phenyl)acrylamide (504.4 mg), and irradiated with ultrasound. Crystalline form obtained in Example 12 was added to the reaction mixture and stirred at room temperature for 7 days. Resultant crystals were filtered off, washed with ethyl acetate (1.5 mL) and dried under reduced pressure for 3 days to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride crystals (565.4 mg).

Figure 14:
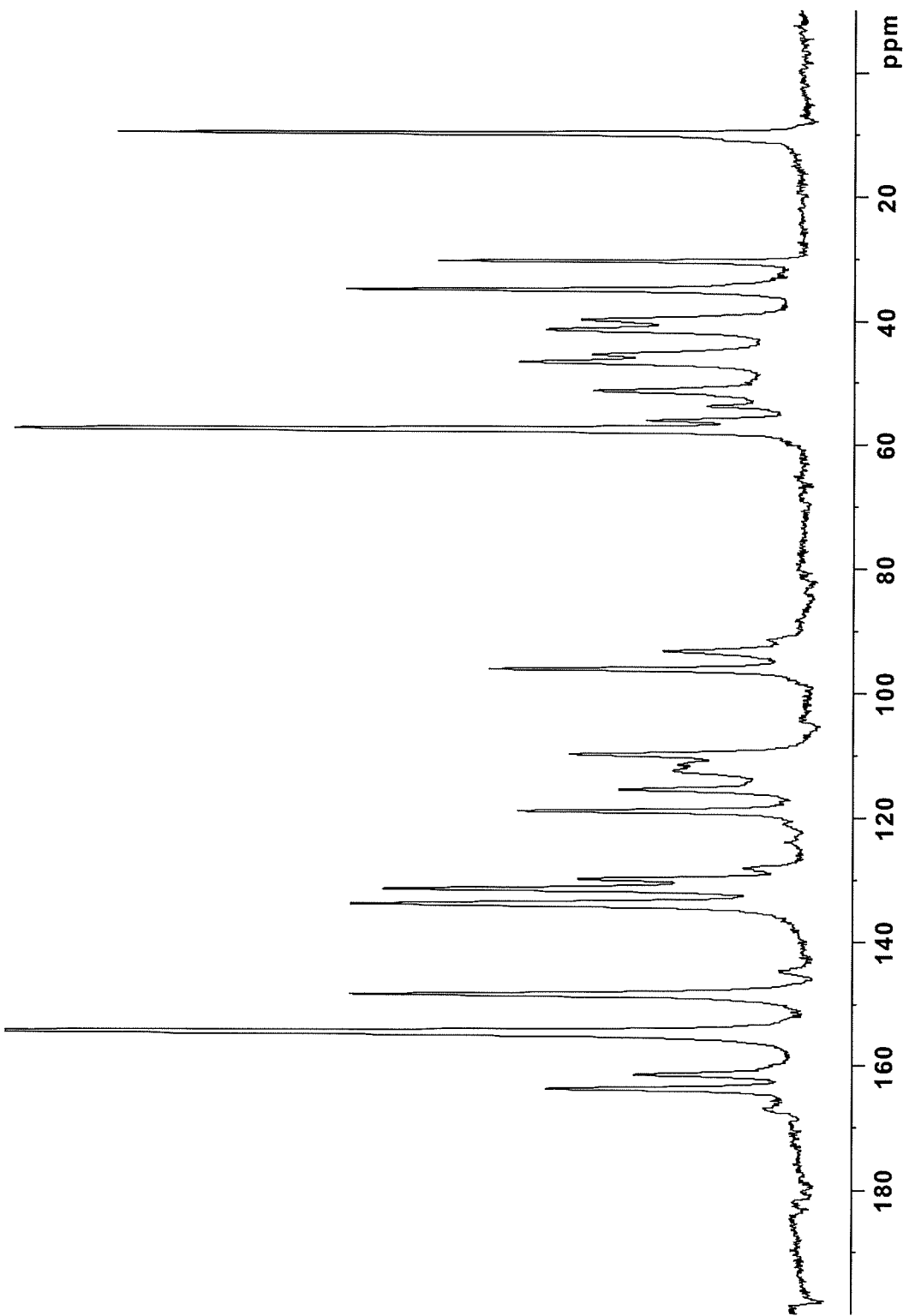
FIG. 14 presents a $^{13}$C-NMR spectrum of crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride (i.e. the crystalline dihydrochloride salt form of Compound 108) obtained in Example 13 herein.

¹³C-NMR (100 MHz, solid state) δ(ppm): 9.9, 30.4, 35.0, 39.8, 41.5, 45.5, 46.7, 51.3, 53.8, 56.1, 57.6, 93.2, 96.1, 109.9, 111.5, 112.5, 115.6, 119.0, 128.2, 130.0, 131.6, 134.0, 148.6, 154.6, 161.4, 163.7. This is shown in FIG. 14.

Figure 15:
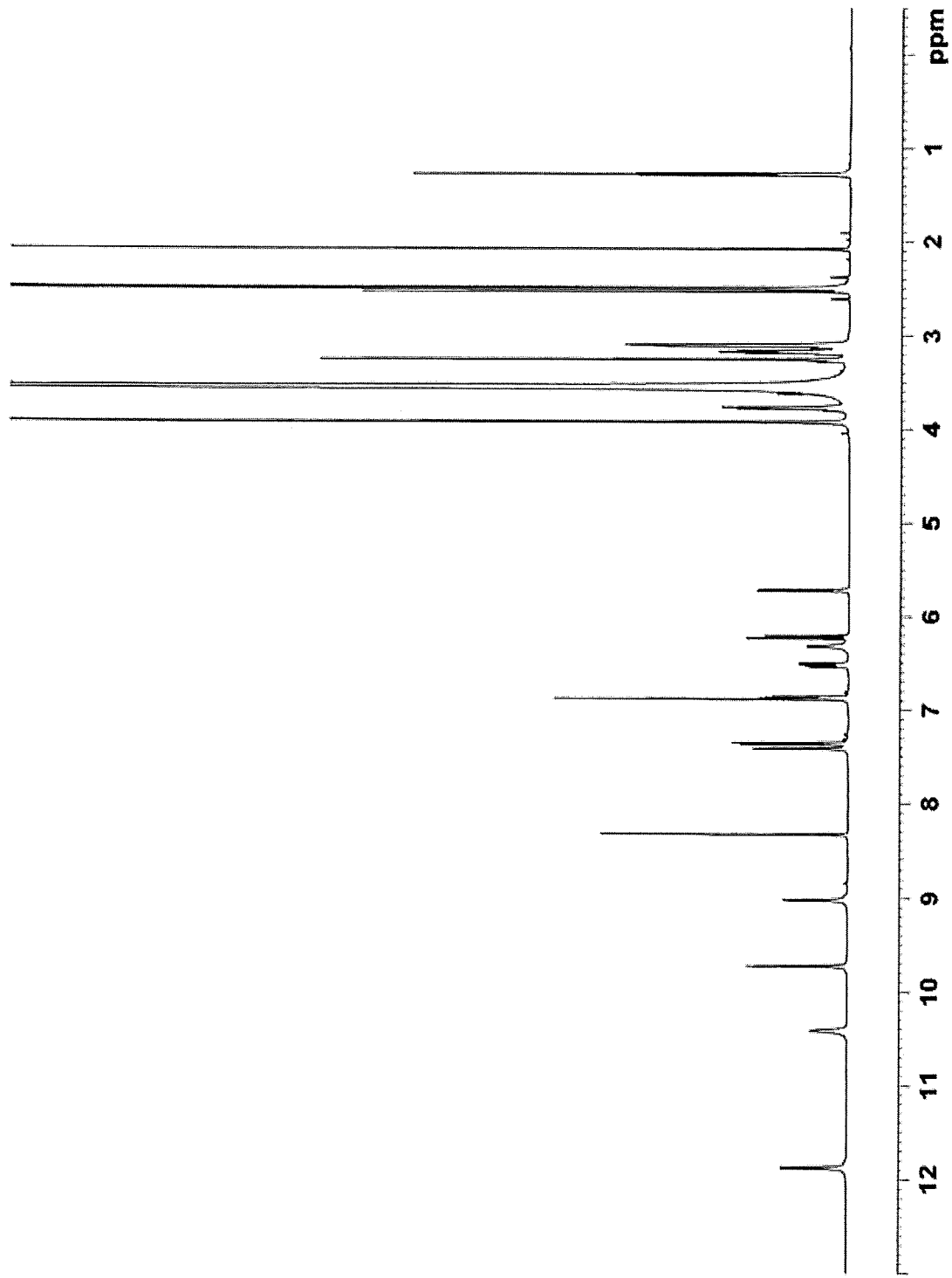
FIG. 15 presents a $^1$H-NMR spectrum of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride obtained in Example 13 herein.

¹H-NMR spectrum (DMSO-d6) δ(ppm): 1.27 (3H, t, J=7.3 Hz), 3.03-3.21 (6H, m), 3.25 (3H, s), 3.52-3.59 (2H, m), 3.72-3.83 (2H, m), 3.92 (6H, s), 5.72 (1H, dd, J=10.3, 1.5 Hz), 6.23 (1H, dd, J=17.1, 1.6 Hz), 6.32 (1H, brs), 6.53 (1H, dd, J=17.0, 10.4), 6.88 (1H, dd, J=8.9, 2.5 Hz), 6.89 (1H, s), 7.37 (1H, d, J=8.8 Hz), 7.42 (1H, brs), 8.34 (1H, s), 9.03 (1H, brs), 9.73 (1H, s), 10.43 (1H, brs), 11.88 (1H, brs). This is shown in FIG. 15.

Example 14

PXRD data for samples in this Example were taken on a Rigaku RINT TTR-III Instrument (Target: Cu; Tube voltage: 50 kV; Tube current: 300 mA, Range 5.0-35.0=30°).

A crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride as prepared in Example 13 is characterized by the PXRD pattern shown in FIG. 16.

As summarized in Table 9, the crystalline form of N-(2-((6-(3-(2,6-dichloro-3,5-dimethoxyphenyl)-1-methylureido)pyrimidin-4-yl)amino)-5-(4-ethylpiperazin-1-yl)phenyl) acrylamide dihydrochloride exhibits a PXRD pattern with at least ten characteristic peaks.

TABLE 9

Characteristic crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide dihydrochloride PXRD Peaks. 2θ° (±0.2°)

| |
|---|
| 8.0 |
| 12.4 |
| 13.5 |
| 16.1 |
| 18.7 |
| 21.3 |
| 22.8 |
| 26.2 |
| 26.6 |
| 28.0 |

Example 15: Preparation of N-(2-((6-(3-(2,6-Dichloro-3,5-Dimethoxyphenyl)-1-methylureido)pyrimidin-4-yl)amino)-5-(4-ethylpiperazin-1-yl)phenyl)acrylamide ethanesulfonate Acetone (5 mL) was spiked with ethanesulfonic acid solution (13.51 μL, 1 eq), added to N-(2-((6-(3-(2,6-dichloro-3,5-dimethoxyphenyl)-1-methylureido)pyrimidin-4-yl)amino)-5-(4-ethylpiperazin-1-yl)phenyl)acrylamide (100.6 mg), irradiated with ultrasound, and stirred at room temperature for 7 days. Resultant crystals were filtered off to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate crystals (103.7 mg).

Example 16: Preparation of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate Acetone (20 mL) was spiked with ethanesulfonic acid solution (67.22 µL, 1 eq), added to N-(2((6-(3-(2,6-dichloro-3,5-dimethoxyphenyl)-1-methylureido)pyrimidin-4-yl) amino)-5-(4-ethylpiperazin-1-yl)phenyl)acrylamide (500.6 mg), and irradiated with ultrasound. Crystalline form obtained in Example 15 was added to the reaction mixture and stirred at room temperature for 3 days. Resultant crystals were filtered off, washed with ethyl acetate (1.5 mL), and dried under reduced pressure for 3 days to give N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate crystals (562.0 mg).

Figure 17:
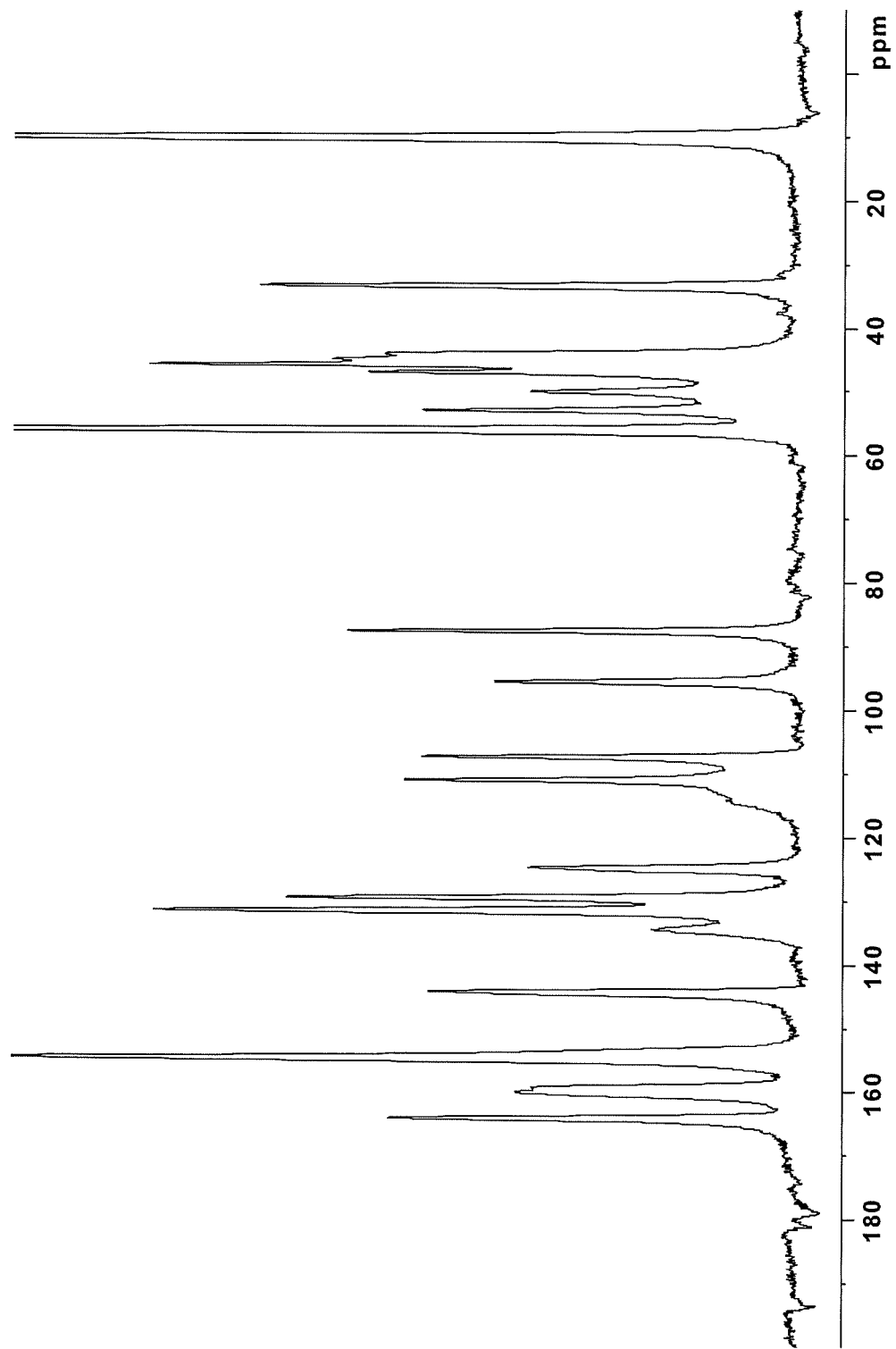
FIG. 17 presents a $^{13}$C-NMR spectrum of crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate (i.e. the crystalline ethanesulfonate salt form of Compound 108) obtained in Example 16 herein.

$^{13}$C-NMR (100 MHz, solid state) δ(ppm): 10.3, 33.4, 44.0, 44.3, 45.0, 45.9, 47.0, 50.0, 53.0, 55.9, 87.6, 95.5, 107.4, 111.0, 124.8, 129.5, 131.5, 134.5, 144.2, 154.6, 159.2, 159.9, 164.1. This is shown in FIG. 17.

Figure 18:
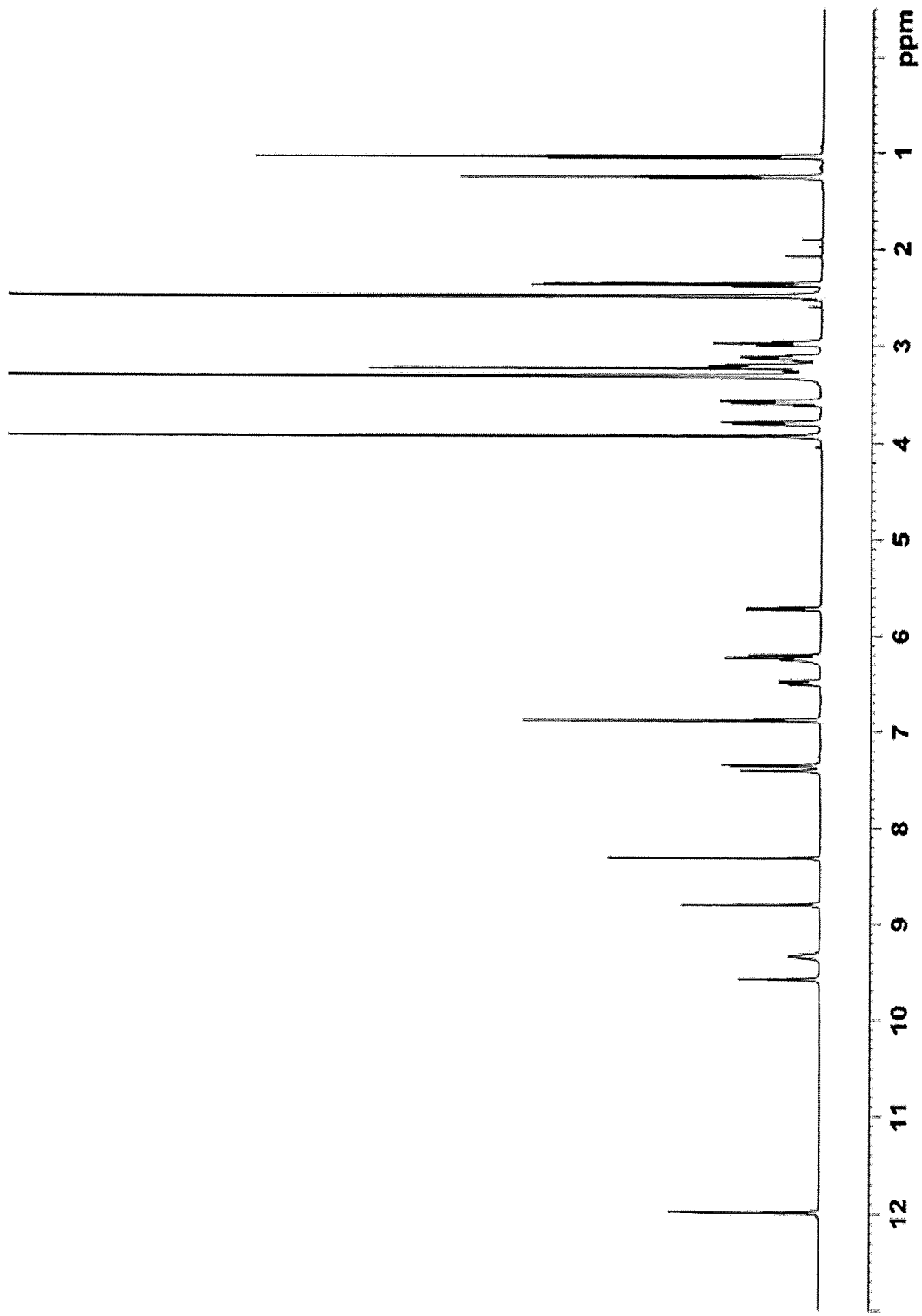
FIG. 18 presents a $^1$H-NMR spectrum of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate obtained in Example 16 herein.

$^1$H-NMR spectrum (DMSO-$d_6$) δ(ppm): 1.05 (3H, t, J=7.5 Hz), 1.25 (3H, t, J=7.3 Hz), 2.37 (2H, q, J=7.4 Hz), 2.98 (2H, t, J=11.7 Hz), 3.13 (2H, m), 3.21 (2H, m), 3.24 (3H, s), 3.58 (2H, brd, J=11.6 Hz), 3.80 (2H, brd, J=12.9 Hz), 3.92 (6H, s), 5.72 (1H, dd, J=10.3, 1.5 Hz), 6.22 (1H, dd, J=17.0, 1.7 Hz), 6.25 (1H, brs), 6.50 (1H, dd, J=17.0, 10.3), 6.84-6.92 (2H, m), 7.36 (1H, d, J=8.9 Hz), 7.41 (1H, brs), 8.32 (1H, s), 8.81 (1H, s), 9.34 (1H, brs), 9.58 (1H, brs), 11.99 (1H, s). This is shown in FIG. 18.

Example 17

PXRD data for samples in this Example were taken on a Rigaku RINT TTR-III Instrument (Target: Cu; Tube voltage: 50 kV; Tube current: 300 mA, Range 5.0-35.0=30°).

A crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate as prepared in Example 16 is characterized by the PXRD pattern shown in FIG. 19.

As summarized in Table 10, the crystalline form of N-(2-((6-(3-(2,6-dichloro-3,5-dimethoxyphenyl)-1-methylureido)pyrimidin-4-yl)amino)-5-(4-ethylpiperazin-1-yl) phenyl)acrylamide ethanesulfonate exhibits a PXRD pattern with at least ten characteristic peaks.

TABLE 10

| Characteristic crystalline N-(2-((6-(3-(2,6-dichloro-3,5-dimethoxyphenyl)-1-methylureido)pyrimidin-4-yl)amino)-5-(4-ethylpiperazin-1-yl)phenyl)acrylamide ethanesulfonate PXRD Peaks. 2θ° (±0.2°) |
| --- |
| 9.4 |
| 11.2 |
| 15.1 |
| 19.2 |
| 20.3 |
| 21.8 |
| 22.4 |
| 23.3 |
| 23.6 |
| 24.0 |

The foregoing is illustrative of the present invention, and is not to be construed as limiting thereof. The invention is defined by the following claims, with equivalents of the claims to be included therein.

We claim:

1. A method for preparing the crystalline free base form of the following compound, comprising:

a) providing a composition comprising a compound:

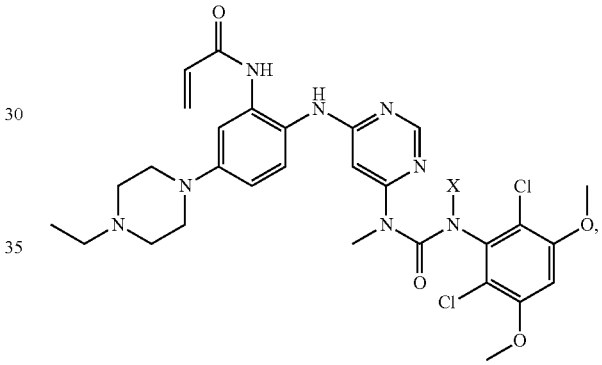

wherein X is (2-(trimethylsilyl)ethoxy)methyl, in a solvent;

b) adding an acid to said composition while maintaining a temperature of the composition ≤50° C.; then c) adding to the composition saturated ammonium hydroxide solution; and then e) extracting the composition with a mixture of immiscible solvents to form an organic phase; and f) adding a suitable solvent to the organic phase, to thereby form said crystalline free base form.

2. The process of claim 1, wherein said acid of step b) is trifluoroacetic acid, hydrochloric acid, hydrobromic acid, sulfuric acid or methanesulfonic acid.

3. The process of claim 1, wherein the suitable solvent of step f) is dichloromethane, acetonitrile, 1,2-dichloroethane, or aqueous dimethyl formamide.

* * * * *